United States Patent
Alemi et al.

(10) Patent No.: US 11,455,753 B1
(45) Date of Patent: Sep. 27, 2022

(54) SYSTEMS AND METHODS TO PROCESS ELECTRONIC IMAGES TO ADJUST ATTRIBUTES OF THE ELECTRONIC IMAGES

(71) Applicant: PAIGE.AI, Inc., New York, NY (US)

(72) Inventors: Navid Alemi, Coventry (GB); Christopher Kanan, Pittsford, NY (US); Leo Grady, Darien, CT (US)

(73) Assignee: PAIGE.AI, Inc., New York, NY (US)

( * ) Notice: Subject to any disclaimer, the term of this patent is extended or adjusted under 35 U.S.C. 154(b) by 0 days.

(21) Appl. No.: 17/643,036

(22) Filed: Dec. 7, 2021

Related U.S. Application Data

(63) Continuation of application No. 17/457,962, filed on Dec. 7, 2021.

(Continued)

(51) Int. Cl.
*G06T 11/00* (2006.01)
*G16H 10/40* (2018.01)
(Continued)

(52) U.S. Cl.
CPC .............. *G06T 11/001* (2013.01); *G06N 20/00* (2019.01); *G06T 7/11* (2017.01); *G16H 10/40* (2018.01);
(Continued)

(58) Field of Classification Search
CPC ......... G06T 7/0012; G06T 2207/10056; G06T 7/90; G06T 3/40; G06T 5/00; G06T 2200/24; G06T 2207/20092
See application file for complete search history.

(56) References Cited

U.S. PATENT DOCUMENTS 5,907,629 A * 5/1999 Funt ..................... H04N 1/6086
382/156
6,165,734 A * 12/2000 Garini ....................... G01J 3/12
435/14

(Continued)

FOREIGN PATENT DOCUMENTS

WO 2019025533 A1 2/2019

OTHER PUBLICATIONS

Chang, Youngha & Saito, Suguru & Uchikawa, Keiji & Nakajima, Masayuki. (2005). Example-Based Color Stylization of Images. TAP. 2. 322-345. 10.1145/1077399.1077408. (Year: 2005).*

(Continued)

*Primary Examiner* — Gandhi Thirugnanam
(74) *Attorney, Agent, or Firm* — Bookoff McAndrews, PLLC

(57) ABSTRACT

Systems and methods are disclosed for adjusting attributes of whole slide images, including stains therein. A portion of a whole slide image comprised of a plurality of pixels in a first color space and including one or more stains may be received as input. Based on an identified stain type of the stain(s), a machine-learned transformation associated with the stain type may be retrieved and applied to convert an identified subset of the pixels from the first to a second color space specific to the identified stain type. One or more attributes of the stain(s) may be adjusted in the second color space to generate a stain-adjusted subset of pixels, which are then converted back to the first color space using an inverse of the machine-learned transformation. A stain-adjusted portion of the whole slide image including at least the stain-adjusted subset of pixels may be provided as output.

20 Claims, 15 Drawing Sheets

Related U.S. Application Data

(60) Provisional application No. 63/187,685, filed on May 12, 2021.

(51) Int. Cl.
- *G16H 70/60* (2018.01)
- *G16H 30/40* (2018.01)
- *G06N 20/00* (2019.01)
- *G06T 7/11* (2017.01)

(52) U.S. Cl.
CPC ............ *G16H 30/40* (2018.01); *G16H 70/60* (2018.01); *G06T 2200/24* (2013.01); *G06T 2207/10024* (2013.01); *G06T 2207/10056* (2013.01); *G06T 2207/20081* (2013.01); *G06T 2207/30024* (2013.01); *G06T 2210/41* (2013.01)

(56) References Cited

U.S. PATENT DOCUMENTS

| | | | | |
|---|---|---|---|---|
| 6,546,123 B1* | 4/2003 | McLaren | | G02B 21/367 |
| | | | | 382/128 |
| 6,580,835 B1* | 6/2003 | Gallagher | | G06T 7/12 |
| | | | | 358/475 |
| 8,454,507 B2* | 6/2013 | Tremper | | A61B 5/4821 |
| | | | | 600/529 |
| 9,159,129 B2* | 10/2015 | Schoenmeyer | | G06T 7/0012 |
| 10,937,541 B2* | 3/2021 | Ceballos Lentini | | G06T 7/0012 |
| 11,062,801 B2* | 7/2021 | Ceballos Lentini | | G06K 9/6256 |
| 2002/0186875 A1* | 12/2002 | Burmer | | G06V 20/69 |
| | | | | 382/133 |
| 2002/0196970 A1* | 12/2002 | Sano | | G06T 9/007 |
| | | | | 382/166 |
| 2003/0206665 A1* | 11/2003 | Pettigrew | | G06F 3/04815 |
| | | | | 382/284 |
| 2006/0200259 A1* | 9/2006 | Hoffberg | | H04N 5/782 |
| | | | | 700/86 |
| 2007/0281734 A1* | 12/2007 | Mizrachi | | H04M 1/24 |
| | | | | 455/550.1 |
| 2008/0159626 A1* | 7/2008 | Ramsay | | G06K 9/00 |
| | | | | 382/162 |
| 2008/0273788 A1* | 11/2008 | Soenksen | | G16H 30/20 |
| | | | | 382/133 |
| 2009/0235193 A1* | 9/2009 | Bhatt | | G06F 3/04847 |
| | | | | 715/765 |
| 2010/0007727 A1* | 1/2010 | Torre-Bueno | | G01N 21/6458 |
| | | | | 382/162 |
| 2010/0329535 A1* | 12/2010 | Macenko | | G06T 7/90 |
| | | | | 382/133 |
| 2012/0076390 A1* | 3/2012 | Potts | | G06T 7/38 |
| | | | | 382/133 |
| 2013/0071002 A1* | 3/2013 | Otsuka | | G06T 7/0012 |
| | | | | 382/133 |
| 2016/0098590 A1* | 4/2016 | Bredno | | G06T 7/0014 |
| | | | | 382/133 |
| 2017/0323148 A1* | 11/2017 | Sarkar | | G06T 7/0012 |
| 2017/0323431 A1* | 11/2017 | Sarkar | | G06T 5/003 |
| 2018/0144464 A1* | 5/2018 | Ben-Dor | | G06T 7/0012 |
| 2018/0260974 A1* | 9/2018 | Cameron | | G06V 10/56 |
| 2018/0349554 A1* | 12/2018 | Jackson | | G06F 40/174 |
| 2019/0019311 A1* | 1/2019 | Hu | | G06T 7/90 |
| 2019/0355113 A1* | 11/2019 | Wirch | | G06V 20/695 |
| 2020/0167965 A1* | 5/2020 | Chukka | | G06V 10/40 |
| 2020/0279126 A1* | 9/2020 | Nie | | G16H 30/40 |
| 2020/0381104 A1* | 12/2020 | Ceballos Lentini | | G16H 50/20 |
| 2020/0387713 A1* | 12/2020 | Kanthan | | G06V 10/82 |
| 2022/0051403 A1* | 2/2022 | Kanan | | G06K 9/6256 |

OTHER PUBLICATIONS

Ruifrok A C et al: Quantification of Histochemical Staining by Color Deconvolution', Analytical and Quantitative Cytology and Histology, Science Printers and Publishers, Inc, US, vol. 23, No. 4, Aug. 1, 2001 (Aug. 1, 2001), pp. 291-299, XP009031319, ISSN: 0884-6812.

Zheng Yushan et al: Adaptive color deconvolution for histological WSI normalization', Computer Methods and Programs in Biomedicine, vol. 170, Mar. 30, 2019 (Mar. 30, 2019), pp. 107-120, XP085594684, ISSN: 0169-2607, DOI: 10.1016/J.CMPB.2019.01.008.

* cited by examiner

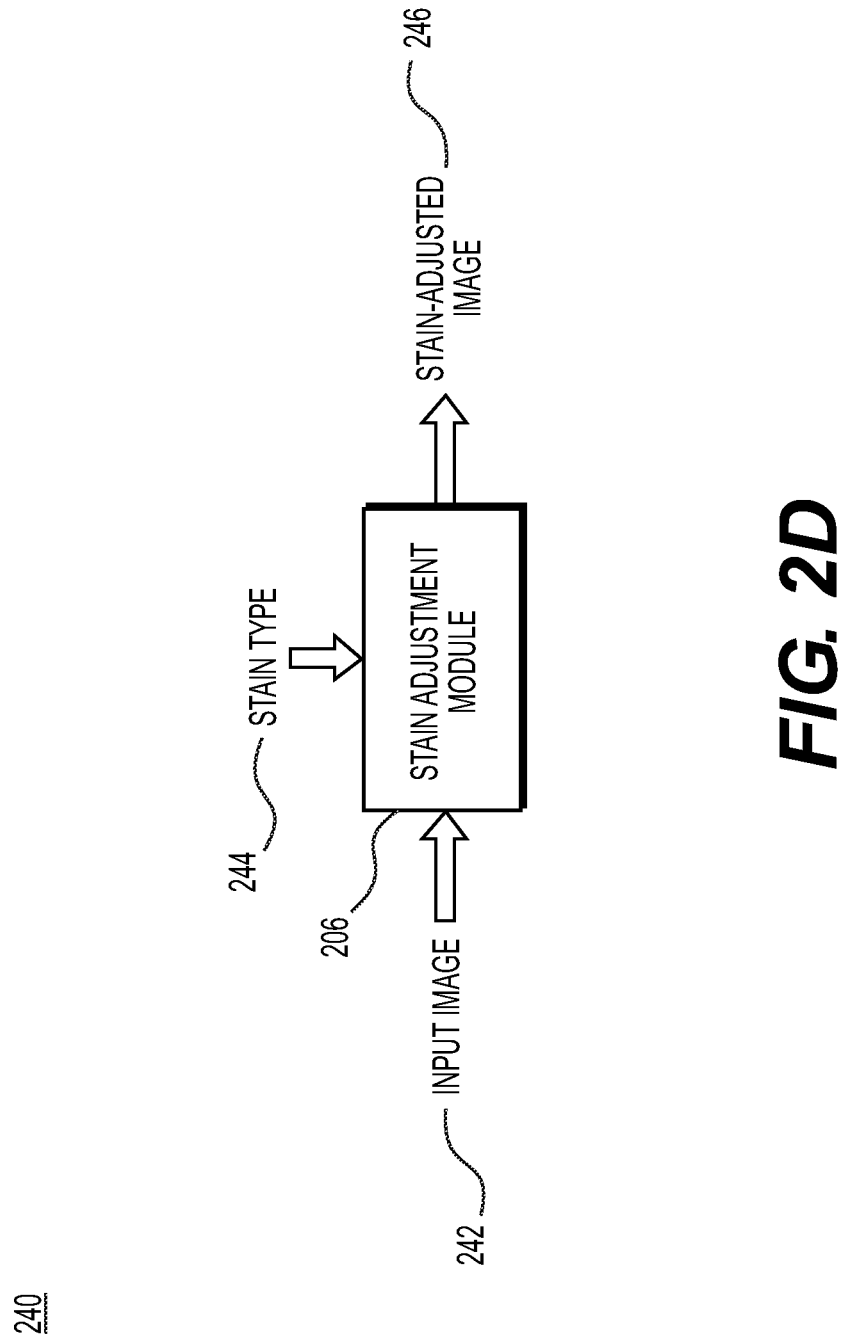

SYSTEMS AND METHODS TO PROCESS ELECTRONIC IMAGES TO ADJUST ATTRIBUTES OF THE ELECTRONIC IMAGES

RELATED APPLICATION(S)

This application is a continuation of and claims priority to U.S. Non-provisional patent application Ser. No. 17/457,962, filed on Dec. 7, 2021, which claims priority to U.S. Provisional Application No. 63/187,685 filed May 12, 2021, the entire disclosures of which are hereby incorporated by reference in their entireties.

FIELD OF THE DISCLOSURE

Various embodiments of the present disclosure pertain generally to image processing methods. More specifically, particular embodiments of the present disclosure relate to systems and methods for adjusting attributes of digital whole slide images.

BACKGROUND

When pathologists review an image of a pathology slide on a microscope, they cannot adjust attributes (e.g., the global or local properties) of that image beyond magnification. With digital pathology, a pathologist may be given tools to alter semantically meaningful, attributes of a digital whole slide image, including one or more stains used to prepare the slide.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for adjusting one or more attributes of whole slide images, including stain adjustment.

A system for adjusting stains in whole slide images may comprise at least a data store storing a plurality of machine-learned transformations associated with a plurality of stain types, a processor, and a memory coupled to the processor and storing instructions. The instructions, when executed by the processor, may cause the system to perform operations including: receiving a portion of a whole slide image comprised of a plurality of pixels in a first color space and including one or more stains, identifying a stain type of the one or more stains, retrieving, from the plurality of stored machine-learned transformations, a machine-learned transformation associated with the identified stain type, identifying a subset of pixels from the plurality of pixels to be transformed, applying the machine-learned transformation to the subset of pixels to convert the subset of pixels from the first color space to a second color space specific to the identified stain type, adjusting one or more attributes of the one or more stains in the second color space to generate a stain-adjusted subset of pixels, converting the stain-adjusted subset of pixels from the second color space to the first color space using an inverse of the machine-learned transformation, and providing, as output, a stain-adjusted portion of the whole slide image including at least the stain-adjusted subset of pixels.

A method for adjusting stains in whole slide images may include: receiving a portion of a whole slide image comprised of a plurality of pixels in a first color space and including one or more stains, identifying a stain type of the one or more stains, retrieving, from a plurality of stored machine-learned transformations associated with a plurality of stain types, a machine-learned transformation associated with the identified stain type, identifying a subset of pixels from the plurality of pixels to be transformed, applying the machine-learned transformation to the subset of pixels to convert the subset of pixels from the first color space to a second color space specific to the identified stain type, adjusting one or more attributes of the one or more stains in the second color space to generate a stain-adjusted subset of pixels, converting the stain-adjusted subset of pixels from the second color space to the first color space using an inverse of the machine-learned transformation, and providing, as output, a stain-adjusted portion of the whole slide image including at least the stain-adjusted subset of pixels.

A non-transitory computer-readable medium may store instructions that, when executed by a processor, cause the processor to perform operations for adjusting stains in whole slide images. The operations may include: receiving a portion of a whole slide image comprised of a plurality of pixels in a first color space and including one or more stains, identifying a stain type of the one or more stains, retrieving, from a plurality of stored machine-learned transformations associated with a plurality of stain types, a machine-learned transformation associated with the identified stain type, identifying a subset of pixels from the plurality of pixels to be transformed, applying the machine-learned transformation to the subset of pixels to convert the subset of pixels from the first color space to a second color space specific to the identified stain type, adjusting one or more attributes of the one or more stains in the second color space to generate a stain-adjusted subset of pixels, converting the stain-adjusted subset of pixels from the second color space to the first color space using an inverse of the machine-learned transformation, and providing, as output, a stain-adjusted portion of the whole slide image including at least the stain-adjusted subset of pixels.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated into and constitute a part of this specification, illustrate various exemplary embodiments and together with the description, serve to explain the principles of the disclosed embodiments.

FIG. 2D is a block diagram illustrating a stain adjustment module trained to adjust stain-specific attributes of a whole slide image, according to an exemplary embodiment of the present disclosure.

DESCRIPTION OF THE EMBODIMENTS

Figure 1A:
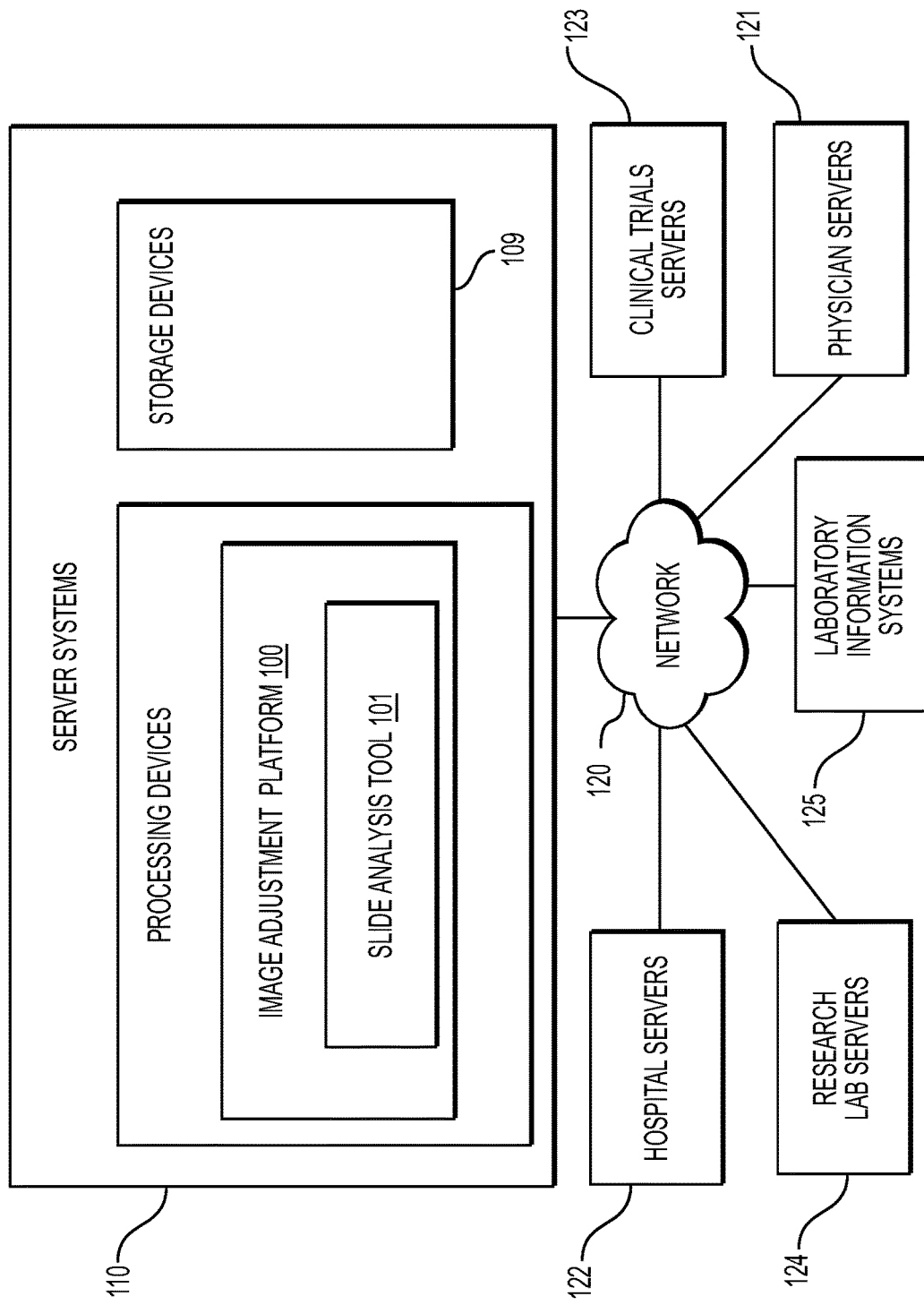
FIG. 1A illustrates an exemplary block diagram of a system and network to adjust attributes of whole slide images, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

In human and animal pathology, visual examination of tissues (histology) and cells (cytology) under a microscope may be a vital element of diagnostic medicine. For example, histology and cytology may be performed to diagnose cancer, facilitate drug development, and assess toxicity, etc. For histology, tissue samples undergo multiple preparation steps so that different tissue structures can be differentiated visually by the human eye when viewing under the microscope. For example, tissue preparation may consist of the following steps: (i) preserving the tissue using fixation; (ii) embedding the tissue in a paraffin block; (iii) cutting the paraffin block into thin sections (3-5 micrometers (μm)); (iv) mounting the sections on glass slides; and/or (v) staining mounted tissue sections to highlight particular components or structures. Tissue preparation may be done manually and hence may introduce large variability into the images observed.

Staining aids in creating visible contrast of the different tissue structures for differentiation by a pathologist. During this process, one or more types of chemical substances (e.g., stains or dyes) are attached to different compounds in the tissue delineating different cellular structures. Different types of stains may highlight different structures. Therefore, pathologists may interpret or analyze the stains differently. Depending on a disease and its underlying behavior, one stain or a combination of stains may be preferable over others for use in diagnostic detection. Although standard protocols for using these stains are often in place, protocols vary per institution and overstaining or understaining of tissue may occur, which may potentially cause diagnostic information or indicators to be obscured. For example, color variations resulting from non-uniform staining between slides may cause one image to look pinker among other images that a pathologist has been reviewing during a day. Such out of distribution images might be hard for the pathologist to investigate as separating different structures might be confusing. For instance, a main characteristic of lymphocytes in Hematoxylin and Eosin (H&E) stained images is their dark purple color; however, in some poorly stained images they might have similar color as other cells. Moreover, multiple stains are commonly used together for highlighting several structures of interest in the tissue, e.g., tissue that is stained with both hematoxylin and eosin, which may further exacerbate potential problems caused by overstaining or understaining.

When pathologists view slides with a traditional microscope, they do not have the ability to alter attributes (e.g., characteristics or properties) of the image produced by the microscope beyond magnification. However, when whole slide imaging is used to scan images of the slides for generating digital whole slide images, image processing and AI-enabled tools may be utilized for adjusting a color, an amount of a particular stain, a brightness, a sharpness, and/or a contrast, among other attribute adjustments to the whole slide images. Such adjustments may enable pathologists to better analyze tissue samples from human or animal patients by allowing them to adjust the image attributes in semantically meaningful ways (e.g., to normalize color across a population of slides being viewed, correct for overstaining or understaining, enhance differentiation of structures, remove artifacts, etc.).

Techniques discussed herein may use AI technology, machine learning, and image processing tools to enable pathologists to adjust digital images according to their needs. Techniques presented herein may be used as part of a visualization software that pathologists use to view the digital whole slide images in their routine workflow. Techniques discussed herein provide methods for enabling adjustments of semantically meaningful image attributes in pathology images, including methods for automatically predicting stain types for use as input in adjustment processes, color normalization methods to enable template-based attribute matching, methods for automatically converting images to particular color spaces in which the semantically meaningful adjustments can be made, and user-interface based methods for enabling attribute value adjustments.

FIG. 1A illustrates an exemplary block diagram of a system and network to adjust attributes of whole slide images, according to an exemplary embodiment of the present disclosure.

Specifically, FIG. 1A illustrates an electronic network 120 that may be connected to servers at hospitals, laboratories, and/or doctor's offices, etc. For example, physician servers 121, hospital servers 122, clinical trial servers 123, research lab servers 124, and/or laboratory information systems 125, etc., may each be connected to an electronic network 120, such as the Internet, through one or more computers, servers and/or handheld mobile devices. According to an exemplary embodiment of the present application, the electronic network 120 may also be connected to server systems 110, which may include processing devices that are configured to implement an image adjustment platform 100, which includes a slide analysis tool 101 for using machine learning and/or image processing tools to identify and adjust one or more attributes of whole slide images, according to an exemplary embodiment of the present disclosure. The slide analysis tool 101 may allow automatic and/or manual adjustments to color, including template-based color matching, an amount of a particular stain, a brightness, a sharpness, and a contrast, among other adjustments.

Image Attribute Adjustments

Examples of whole slide images may include digitized images of histology or cytology slides stained with a variety of stains, such as, but not limited to, hematoxylin and eosin, hematoxylin alone, toluidine blue, alcian blue, Giemsa, trichrome, acid-fast, Nissl stain, etc. Non-limiting and non-exhaustive uses of each stain or combination of stains and implementation of the image adjustment platform 100 for enhancing the viewing and analysis of whole slide images including these stain(s) are described briefly below.

Adjustments of Colors in Image Stained with Hematoxylin and Eosin

Hematoxylin and Eosin are the most commonly used stains for morphological analysis of tissue. Hematoxylin binds to deoxyribonucleic acid (DNA) and stains the nuclei dark blue or purple, whereas eosin stains the extracellular matrix and cytoplasm pink. The image adjustment platform 100 may be used for adjustment (e.g., correction) of over-staining or under-staining of hematoxylin or eosin.

Adjustment of Blue and Purple Color in Toluidine Blue Stained Image

Toluidine blue is a polychromatic dye which may absorb different colors depending on how it binds chemically with various tissue components. In diagnostic labs, toluidine blue may be used by pathologists to highlight mast cell granules, particularly when evaluating patients with pathological conditions that involve mast cells (including cancers), allergic inflammatory diseases, and gastrointestinal diseases such as irritable bowel syndrome. Toluidine blue may also be used to highlight tissue components such as cartilage or certain types of mucin. Further, toluidine blue may be used as part of the screening process for certain cancers, such as oral cancer, as it binds the DNA of dividing cells causing precancerous and cancerous cells to take up more of the dye than healthy cells.

Adjustments of Blue and Pink Color in Alcian Blue Stained Images

The alcian blue stain may cause acid mucins and mucosubstances to appear blue, and nuclei to appear reddish pink when a counterstain of neutral red is used. The blue and pink colors of the stain may be adjusted using the image adjustment platform 100 for better visualization of nuclei and other features in the image.

Adjustments of Purple and Pink in Giemsa Stained Images

A Giemsa stain is a blood stain that may be used histopathologically to observe composition and structure. Additionally, Giemsa has high-quality staining capabilities of chromatin and nuclear membranes. Human and pathogenic cells may be stained differently, where human cells may be stained purple and bacterial cells pink for differentiation. The image adjustment platform 100 may be used to adjust the pink and purple colors to enhance the contrast between human cells and bacterial cells.

Adjustment of Colors in Images with Trichrome Stain

Trichome stains may use three dyes to produce different coloration of different tissue types. Typically, trichrome stains may be used to demonstrate collagen, often in contrast to smooth muscle, but may also be used to highlight fibrin in contrast to red blood cells. The image adjustment platform 100 may be used to adjust green and blue colors to enhance a contrast for collagen and bone. Red and black colors also may be modified by the image adjustment platform 100 to adjust the appearance of nuclei. Further, contrast for nuclei, Musin, fibrin and/or cytoplasm may be changed by adjusting red and yellow colors.

Adjustment of Colors in Images with Acid-Fast Stain

Acid-fast is a differential stain used to identify acid-fast bacterial organisms, such as members of the genus *Mycobacterium* and *Nocardia*. The stain colors bacterial organisms as red-pink and other matter as bluish. The image adjustment platform 100 may be used to adjust colors, including stain colors, and contrast to enhance the visibility of bacteria in the images.

Adjustment of Colors in Images with Nissl Stain

Nissl staining is used to visualize Nissl substance (e.g., clumps of rough endoplasmic reticulum and free polyribosomes) found in neurons. This stain may distinguish neurons from glia and the cytoarchitecture of neurons may be more thoroughly studied with the help of this stain. A loss of Nissl substance may signify abnormalities, such as cell injury or degeneration, which in turn may indicate disease. The image adjustment platform 100 may be used to adjust pink and blue colors produced by the stain to better visualize the difference between various types of neurons.

The Environment

The physician servers 121, hospital servers 122, clinical trial servers 123, research lab servers 124 and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124 and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the one or more storage devices 109. Server systems 110 may further include one or more machine learning tool(s) or capabilities. For example, the processing devices may include one or more machine learning tools for the image adjustment platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124 and/or laboratory information systems 125 refer to systems used by pathologists for reviewing the images of the slides. In hospital settings, tissue type information may be stored in a laboratory information system 125. Additionally, information related to stains used for tissue preparation, including stain type, may be stored in the laboratory information systems 125.

Figure 1B:
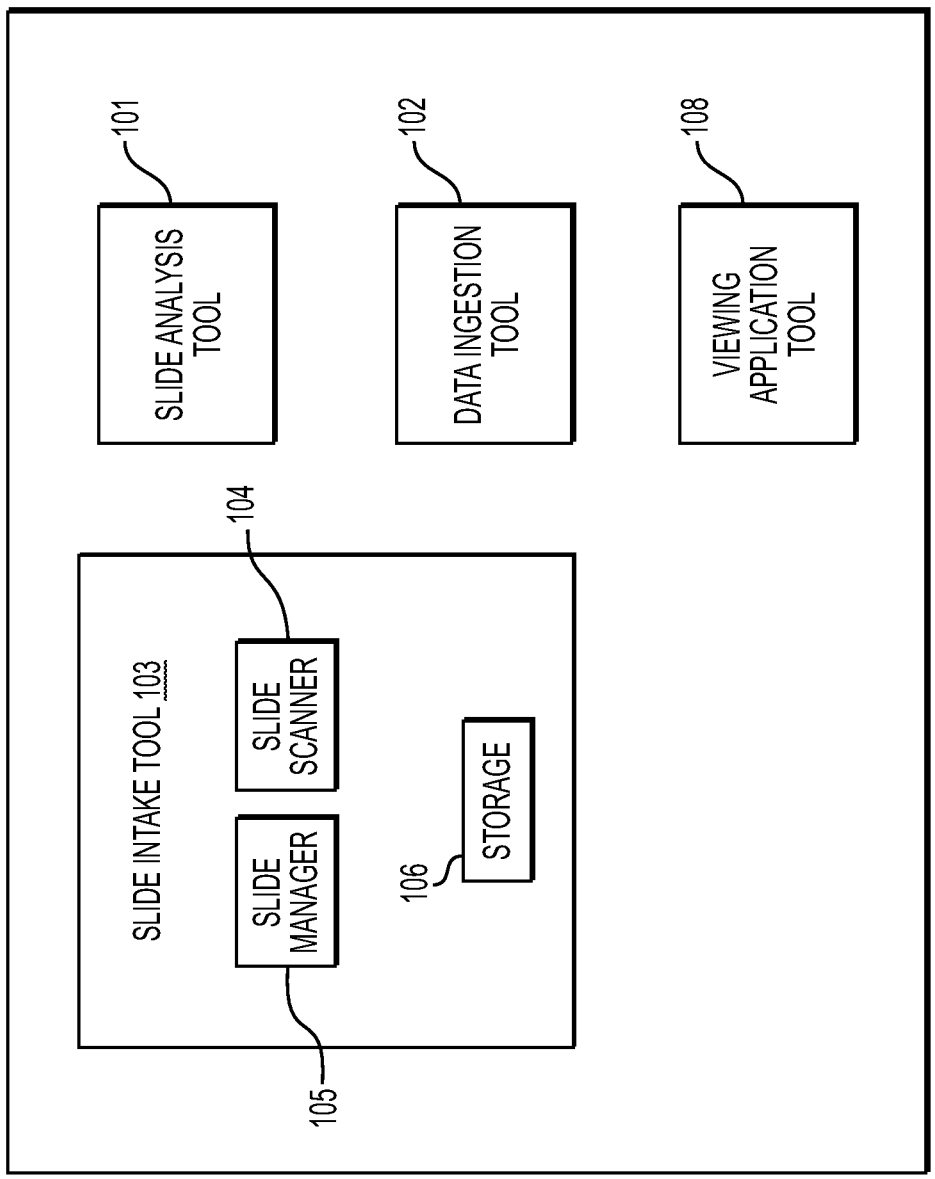
FIG. 1B illustrates an exemplary block diagram of an image adjustment platform, according to an exemplary embodiment of the present disclosure.

FIG. 1B illustrates an exemplary block diagram of the image adjustment platform 100. The image adjustment platform 100 may include a slide analysis tool 101, a data ingestion tool 102, a slide intake tool 103, a slide scanner 104, a slide manager 105, a storage 106, and a viewing application tool 108.

The slide analysis tool 101, as described below, refers to a process and system for identifying and adjusting one or more attributes of whole slide images. Machine learning may be used to predict a stain type of one or more stains present in a whole slide image, according to an exemplary embodiment. Machine learning may also be used for color normalization processes to map color characteristics of a template to the whole slide image for adjusting a color thereof to enable color constancy among images viewed, according to another exemplary embodiment. Machine learning may further be used to convert an original color space of the whole slide image to a color space that is specific to a stain type of one or more stains identified in the whole slide image to enable a brightness or an amount of the one or more stains to be adjusted, according to another exemplary embodiment. The slide analysis tool 101 may also provide graphical user interface (GUI) control elements (e.g., slider bars) for display in conjunction with the whole slide image through a user interface of the viewing application tool 108 to allow user-input based adjustment of attribute values for color, brightness, sharpness, and contrast, among other similar examples, as described in the embodiments below.

The data ingestion tool 102 may facilitate a transfer of the whole slide images to the various tools, modules, components, and devices that are used for classifying and processing the whole slide images, according to an exemplary embodiment. In some examples, if the whole slide image is adjusted utilizing one or more features of the slide analysis tool 101, only the adjusted whole slide image may be transferred. In other examples, both the original whole slide image and the adjusted whole slide image may be transferred.

The slide intake tool 103 may scan pathology slides and convert them into a digital form, according to an exemplary embodiment. The slides may be scanned with slide scanner 104, and the slide manager 105 may process the images on the slides into digitized whole slide images and store the digitized whole slide images in storage 106.

The viewing application tool 108 may provide a user (e.g., pathologist) a user interface that displays the whole slide images throughout various stages of adjustment. The user interface may also include the GUI control elements of the slide analysis tool 101 that may be interacted with to adjust the whole slide images, according to an exemplary embodiment. The information may be provided through various output interfaces (e.g., a screen, a monitor, a storage device and/or a web browser, etc.).

The slide analysis tool 101, and one or more of its components, may transmit and/or receive digitized whole slide images and/or patient information to server systems 110, physician servers 121, hospital servers 122, clinical trial servers 123, research lab servers 124, and/or laboratory information systems 125 over an electronic network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools and modules may be located on a device that may be connected to an electronic network such as the Internet or a cloud service provider, through one or more computers, servers and/or handheld mobile devices.

Figure 1C:
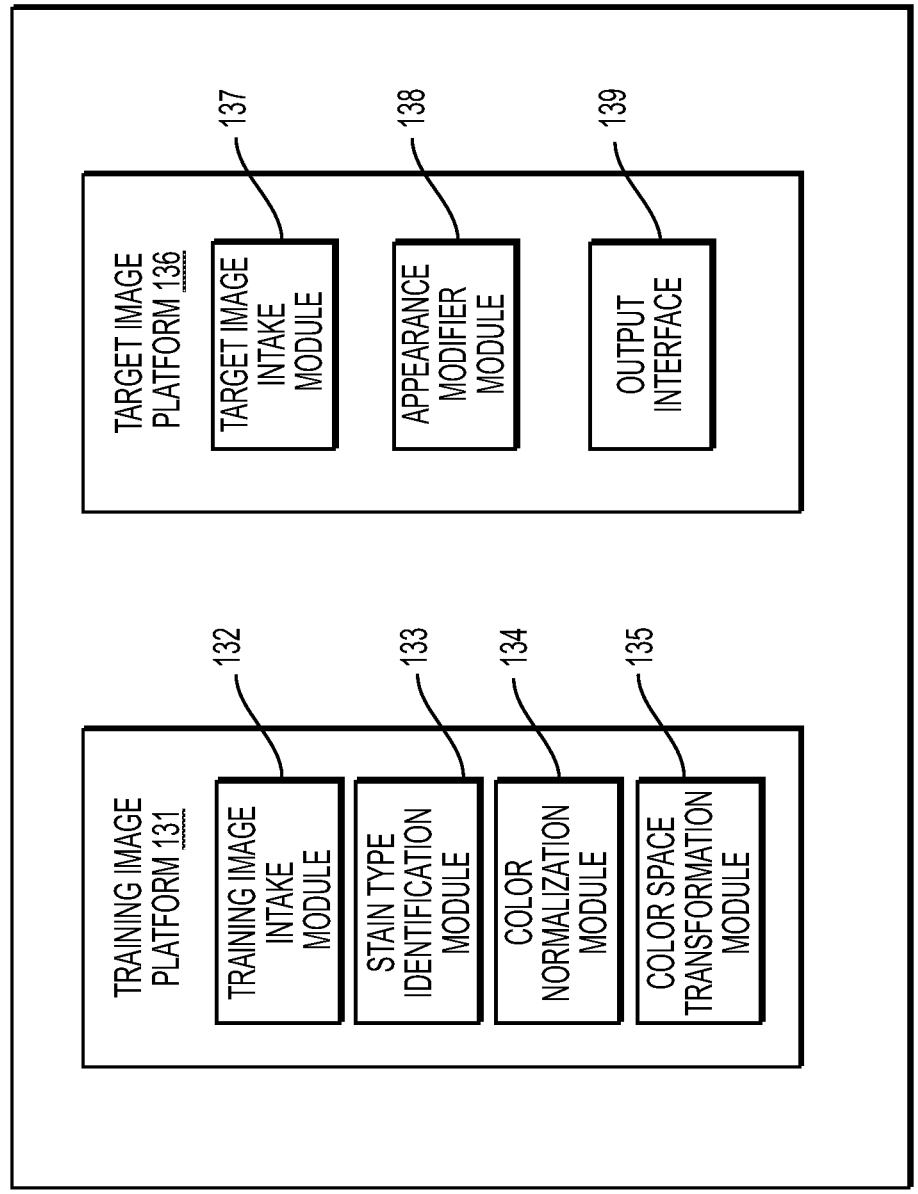
FIG. 1C illustrates an exemplary block diagram of a slide analysis tool, according to an exemplary embodiment of the present disclosure.

FIG. 1C illustrates an exemplary block diagram of a slide analysis tool 101, according to an exemplary embodiment of the present disclosure. The slide analysis tool 101 may include a training image platform 131 and/or a target image platform 136.

According to one embodiment, the training image platform 131 may include a plurality of software modules, including a training image intake module 132, a stain type identification module 133, a color normalization module 134, and a color space transformation module 135.

The training image platform 131, according to one embodiment, may create or receive one or more datasets of training images used to generate and train one or more machine learning models that, when implemented, facilitate adjustments to various attributes of whole slide images. For example, the training images may include whole slide images received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of whole slide images may include digitized histology or cytology slides stained with a variety of stains, such as, but not limited to, Hematoxylin and eosin, hematoxylin alone, toluidine blue, alcian blue, Giemsa, trichrome, acid-fast, Nissl stain, etc.

The training image intake module 132 of the training image platform 131 may create or receive the one or more datasets of training images. For example, the datasets may include one or more datasets corresponding to stain type identification, one or more datasets corresponding to color normalization, and one or more datasets corresponding to stain-specific color space transformation. In some examples, a subset of training images may overlap between or among the various datasets for stain type identification, color normalization, and stain-specific color space transformation. The datasets may be stored on a digital storage device (e.g., one of storages devices 109).

The stain type identification module 133 may generate, using at least the datasets corresponding to stain type identification as input, one or more machine learning systems capable of predicting a stain type of one or more stains present in a whole slide image. The color normalization module 134 may generate, using at least the datasets corresponding to color normalization as input, one or more machine learning systems capable of mapping color characteristics of one whole slide image (e.g., a template) to another whole slide image to provide color constancy between the two whole slide images. The color space transformation module 135 may generate, using at least the datasets corresponding to stain-specific color space transformation as input, one or more machine learning systems capable of identifying transformations for converting a whole slide image in an original color space to a new color space that is specific to a stain type of one or more stains present in the whole slide image to facilitate stain adjustments. In some examples, a machine learning system may be generated for each of the different stain types to learn a corresponding transformation. In other examples, one machine learning system may be generated that is capable of learning transformations for more than one stain type.

According to one embodiment, the target image platform 136 may include software modules, such as a target image intake module 137 and an appearance modifier module 138, in addition to an output interface 139. The target image platform 136 may receive a target whole slide image as input and provide the image to the appearance modifier module 138 to adjust one or more attributes of the target whole slide image. For example, the target whole slide image may be received from any one or any combination of the server systems 110, physician servers 121, hospital servers 122, clinical trial servers 123, research lab servers 124, and/or laboratory information systems 125. The appearance modifier module 138 may be comprised of one or more sub-modules, described in detail with reference to FIGS. 2A through 2E below. The sub-modules may execute the various machine learning models generated by the training image platform 131 to facilitate the adjustments to the attributes of whole slide images. In some aspects, the adjustments may be customizable based on user input.

The output interface 139 may be used to output the adjusted target whole slide image (e.g., to a screen, monitor, storage device, web browser, etc.).

Figure 2A:
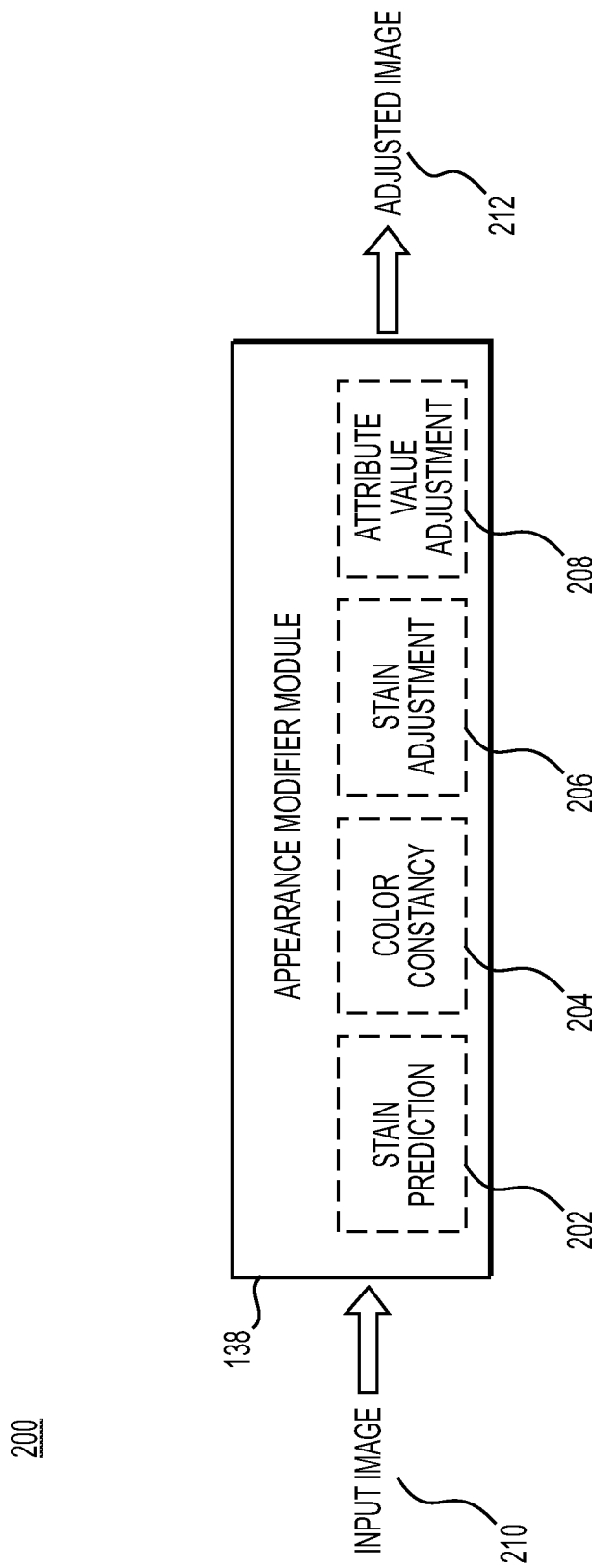
FIG. 2A is a block diagram illustrating an appearance modifier module of a slide analysis tool for adjusting attributes of whole slide images, according to an exemplary embodiment of the present disclosure.

FIG. 2A through FIG. 2E are block diagrams illustrating the appearance modifier module 138 and software sub-modules thereof for adjusting various attributes of a whole slide image. FIG. 2A is a block diagram 200 illustrating the appearance modifier module 138. The appearance modifier module 138 may include one or more software sub-modules, including a stain prediction module 202, a color constancy module 204, a stain adjustment module 206, and an attribute value adjustment module 208. A whole slide image may be received as input (e.g., input image 210) to the appearance modifier module 138. The input image 210 may include a histology whole slide image or a cytology whole slide image, where the whole slide image may be a digitized image of a slide-mounted and stained histology or cytology specimen, for example. Upon receipt of the input image 210, at least one of the sub-modules 202, 204, 206, 208 may be executed, and an adjusted image 212 may be provided as output of the appearance modifier module 138.

The adjusted image 212 may include an adjusted color, an adjusted amount of a particular stain, an adjusted brightness, an adjusted sharpness, and/or adjusted contrast, among other adjustments. In some examples, indications of one or more regions of the input image 210 to be adjusted may also be received as input and only those one or more regions (e.g., rather than the entire image) may be adjusted in the adjusted image 212. Further inputs utilized by (e.g., specific to) one or more of the modules 202, 204, 206, 208, described in detail in FIGS. 2B through 2E below, may be received and applied to adjust the attributes of the input image 210 accordingly.

Figure 2B:
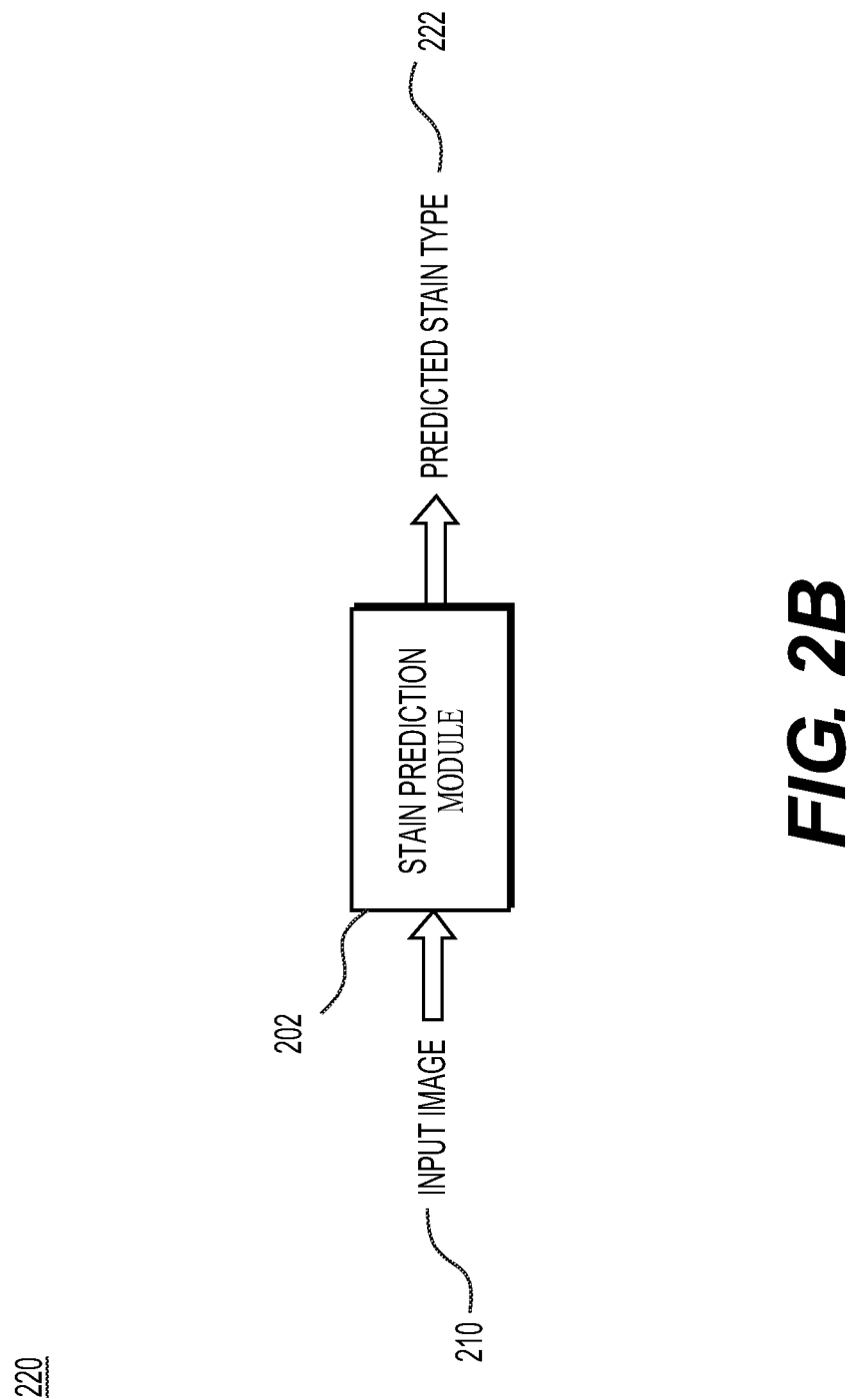
FIG. 2B is a block diagram illustrating a stain prediction module trained to predict a stain type of one or more stains present in a whole slide image, according to an exemplary embodiment of the present disclosure.

FIG. 2B is a block diagram 220 illustrating the stain prediction module 202. The stain prediction module 202 may execute a trained machine learning system for predicting stain types, such as the trained machine learning system generated by the stain type identification module 133. The input image 210 received at the appearance modifier module 138 and subsequently at the stain prediction module 202 may include one or more stains of a particular stain type. In some examples, the input image 210 may be provided without an indication of the stain type (e.g., an input stain type is not received). In such examples, the stain prediction module 202 may execute the trained machine learning system to predict the stain type of the one or more stains present in the input image 210. The predicted stain type 222 output by the trained machine learning system may be provided as output of the stain prediction module 202.

In other examples, an input stain type of the one or more stains may be received along with the input image 210 (e.g., as additional input) to the stain prediction module 202. Nonetheless, the stain prediction module 202 may execute the trained machine learning system to predict the stain type as part of a validation process. For example, the predicted stain type 222 may be compared to the input stain type to determine whether the input stain type is erroneous. In some examples, when the input stain type is determined to be erroneous, a notification or an alert may be provided to a user (e.g., via the viewing application tool 108).

The predicted stain type 222 may be stored in association with the image 210 in a storage device (e.g., one of storage devices 109) at temporarily throughout the attribute adjustment process. In some aspects, the predicted stain type 222 may be used as input to one or more other sub-modules of the appearance modifier module 138, such as the stain adjustment module 206.

Figure 2C:
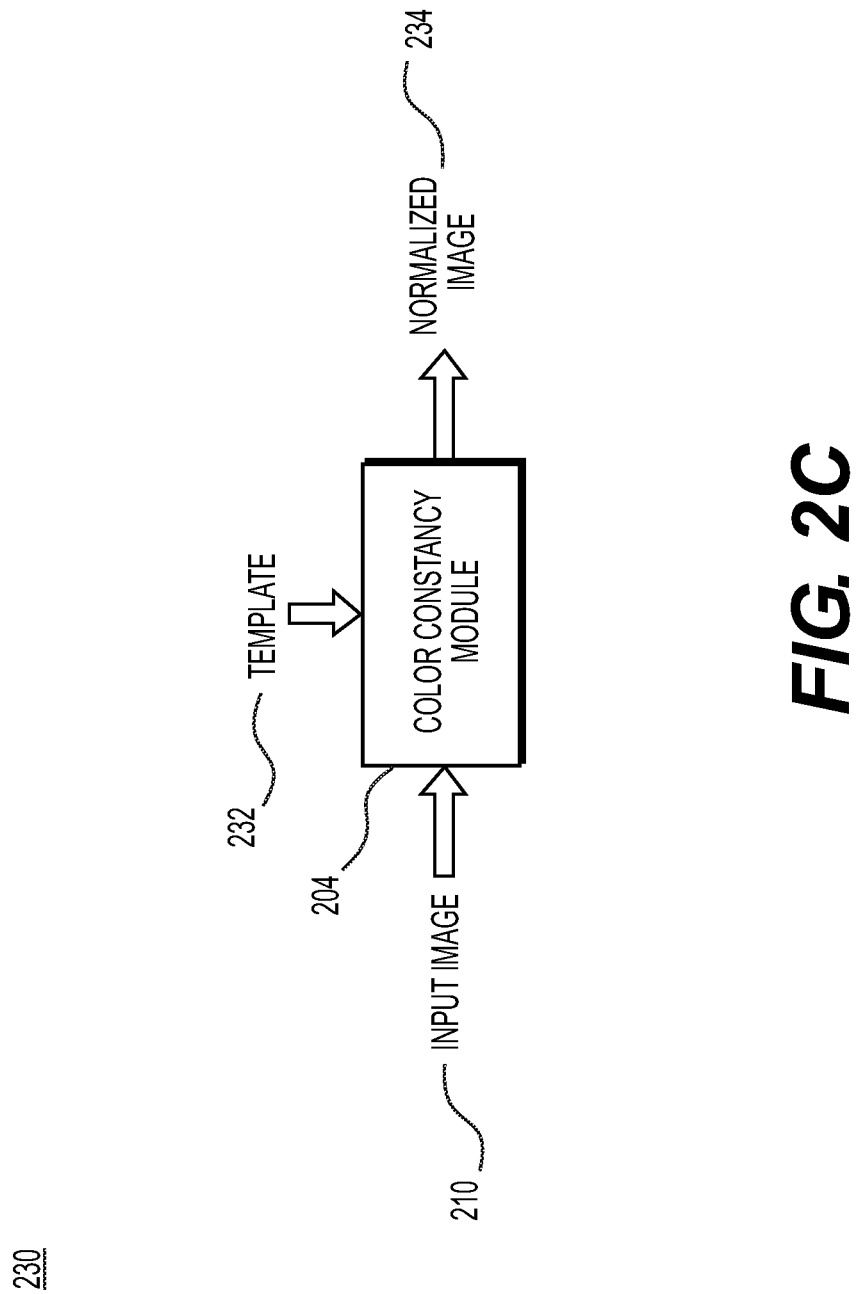
FIG. 2C is a block diagram illustrating a color constancy module trained to provide template-based attribute matching to adjust a whole slide image, according to an exemplary embodiment of the present disclosure.

FIG. 2C is a block diagram 230 illustrating the color constancy module 204. The color constancy module 204 may adjust at least color characteristics of the input image 210 received at the appearance modifier module 138 based on a template 232 comprised of at least a portion of one or more whole slide images that is received as further input. In some examples, the template 232 may be a population of whole slide images, including the image 210, provided as collective input to the appearance modifier module 138. In other examples, the template 232 may include a reference set of whole slide images. In some examples, the input image 210 to be adjusted may be referred to as a source input image and the template 232 may be referred to as a target input image as it is the color characteristics of the template 232 that are the target for mapping onto the input image 210. The color constancy module 204 may use one or more color normalization techniques to enable mapping of the color characteristics from the template 232 to the input image 210 to output a normalized image 234. The color constancy module 204 may execute a trained machine learning system for performing the color normalization, such as the trained machine learning system generated by the color normalization module 134. Additionally and/or alternatively, further adjustments to the color characteristics of the input image 210 may be made based on user-specified information received in addition to the input image 210 and the template 232 as input. In some examples, the attribute value adjustment module 208 may facilitate these further adjustments.

The normalized image 234 having adjusted color characteristics corresponding to the color characteristics of the template 232 and/or user-specified information may be provided as output of the color constancy module 204. In some examples, the normalized image 234 may be provided as input into one or more other sub-modules of the appearance modifier module 138 to cause further adjustments to be made to the normalized image 234. In other examples, the normalized image 234 may be the adjusted image 212 output by the appearance modifier module 138.

FIG. 2D is a block diagram 240 illustrating the stain adjustment module 206. The stain adjustment module 206 may receive an image 242 and a stain type 244 of the image 242 as input. In some examples, the image 242 may be the input image 210 originally received at the appearance modifier module 138. In other examples, the image 242 may be a previously adjusted version of the input image 210 that was output by another one of the sub-modules of the appearance modifier module 138. For instance, the normalized image 234 output by the color constancy module 204. The stain type 244 may be a stain type input by a user (e.g., the pathologist) or otherwise associated with the image 242. Additionally or alternatively, the stain type 244 may be the predicted stain type 222 output by the stain prediction module 202.

The stain adjustment module 206 may adjust properties of the one or more stains present in the image 242 for output as a stain-adjusted image 246. For example, a brightness and/or an amount of the one or more stains may be adjusted. In some aspects, graphical user interface (GUI) control elements, such as slider bars, may be provided to the user to allow the user to interactively define the configuration for controlling the particular stain adjustments. In other aspects, the stains may be adjusted to correspond to a defined configuration for stains within a template. The template may include a population of whole slide images, including the input image 210, provided collectively as input to the appearance modifier module 138. In other examples, the template may include a reference set of whole slide images.

To enable the stain adjustments, the stain adjustment module 206 may convert the image 242 in an original color space (e.g., a red, green, blue (RGB) color space) to a new color space that is specific to the stain type of one or more stains present in the image 242. For example, the stain adjustments according to the defined configuration may be made to the image 242 in the stain-specific color space and then converted back to the original color space for output as the stain-adjusted image 246. To convert the image 242 to the new, stain-specific color space, a transformation learned by a machine learning system, such as one or more of the machine learning systems generated by the color space transformation module 135, may be identified, retrieved, and applied to the image 242.

The stain-adjusted image 246 having the defined configuration may be provided as output of the stain adjustment module 206. In some examples, the stain-adjusted image 246 may be provided as input to one or more other modules, such as the attribute value adjustment module 208. In other examples, the stain-adjusted image 246 may be the adjusted image 212 provided as output of the appearance modifier module 138. As previously discussed, in some examples, the image 242 is the normalized image 234 output by the color constancy module 204 (e.g., rather than the input image 210) and thus the stain-adjusted image 246 output by the stain adjustment module 206 may be a normalized, stain-adjusted image.

Figure 2E:
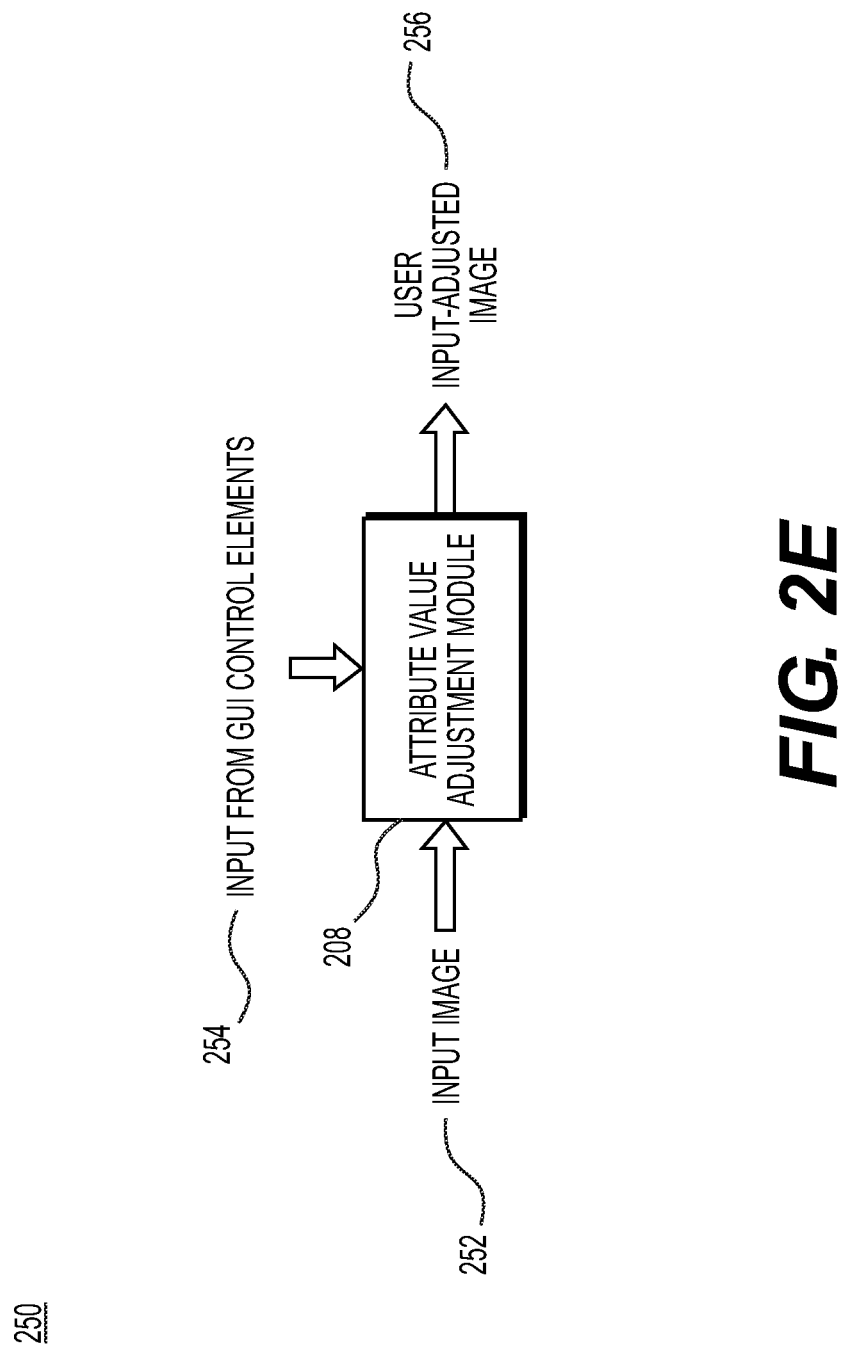
FIG. 2E is a block diagram illustrating an attribute value adjustment module for adjusting values of one or more attributes of a whole slide image based on user input, according to an exemplary embodiment of the present disclosure.

FIG. 2E is a block diagram 250 illustrating the attribute value adjustment module 208. The attribute value adjustment module 208 may receive an image 252 as input. In some examples, the image 252 may be the input image 210 received as input to the appearance modifier module 138. In other examples, the image 252 may be an image output by another one or more of the sub-modules of the appearance modifier module 138. For instance, the image 252 may be the normalized image 234 output by the color constancy module 204 or the stain-adjusted image 246 output by the stain adjustment module 206, where the stain-adjusted image 246 may further be a normalized, stain-adjusted image (e.g., an image previously adjusted by both the color constancy module 204 and the stain adjustment module 206).

The attribute value adjustment module 208 may adjust values of one or more attributes of the image 252 based on user input 254 to generate a user input-adjusted image 256. The adjustable attributes may include color (including hue and saturation), brightness, sharpness, and contrast, among other similar attributes. The user input 254 may be received as user interactions with the plurality of GUI control elements provided in conjunction with the image 252 through the viewing application tool 108. As one specific but non-limiting example, a slider bar may be provided for each of one or more attributes, where user input to or interaction with a given slider bar (e.g., movement from one end to another end) may increase or decrease values associated with the respective attribute. Other control elements that allow incremental increases and decreases of value, similar to a slider bar, may be used in addition or alternatively to a slider bar. In some examples, the user input-adjusted image 256 may be displayed and updated in real-time through the viewing application tool 108 as the user input 254 is received and applied. The user input-adjusted image 256 may be the adjusted image 212 output by the appearance modifier module 138. In other examples, the user input-adjusted image 256 can be provided as input to the other submodules previously discussed.

Figure 3:
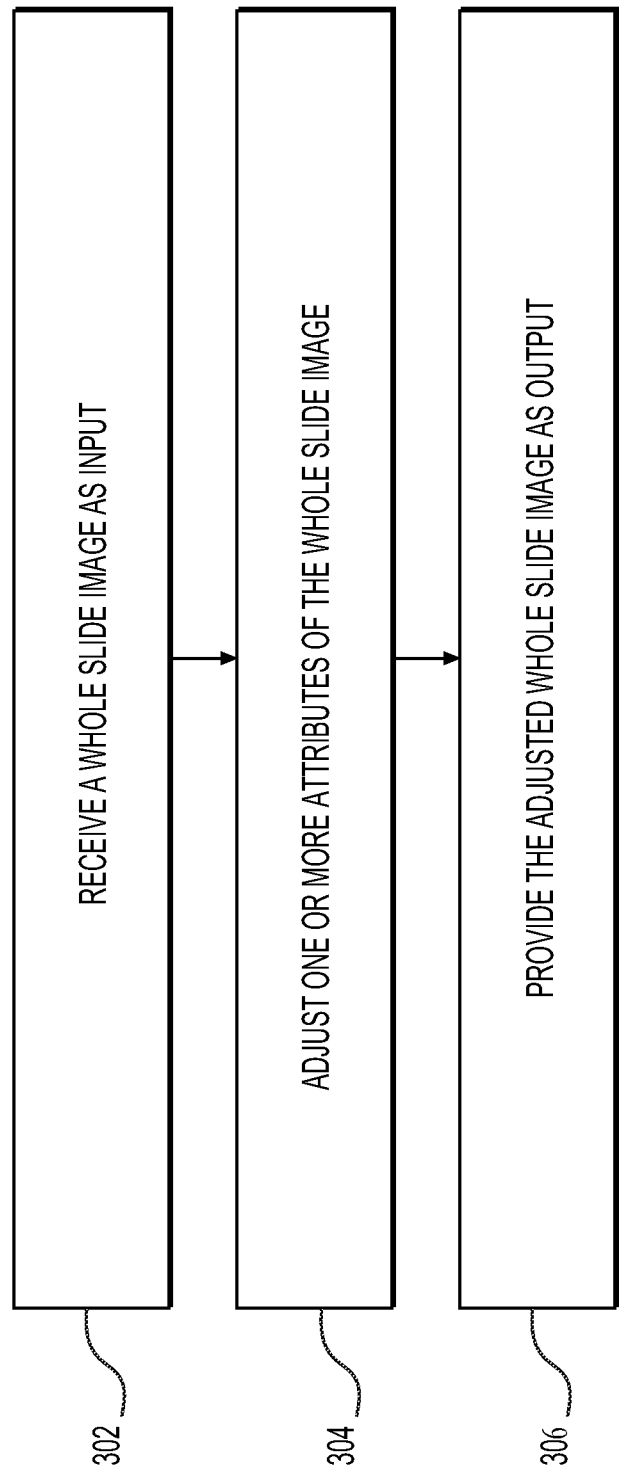
FIG. 3 is a flowchart illustrating an exemplary method for adjusting attributes of a whole slide image, according to an exemplary embodiment of the present disclosure.

FIG. 3 is a flowchart illustrating an exemplary method 300 for adjusting one or more attributes of a whole slide images, according to an exemplary embodiment of the present disclosure. The exemplary method 300 (e.g., steps 302-306) may be performed by the slide analysis tool 101 of the image adjustment platform 100 automatically and/or in response to a request from a user (e.g., pathologist, patient, oncologist, technician, administrator, etc.). The exemplary method 300 may include one or more of the following steps.

In step 302, the method 300 may include receiving a whole slide image as input (e.g., input image 210). The whole slide image may be a digitized image of a slide-mounted histology or cytology specimen, for example. The whole slide image may include one or more stains that were added to the slides to allow differentiation of various tissue or cellular structures by the human eye when imaged. The types of stains added may be dependent on which type of structures are desired to be differentiated. In some examples, only a portion (e.g., one or more regions) of the whole slide image may be received as input. The portion may include one or more regions or areas of interest. In such examples, the remaining steps 304 and 306 may be performed on the portion of the whole slide image rather than an entirety of the whole slide image.

In step 304, the method 300 may include adjusting one or more attributes of the whole slide image. The attributes may be visual attributes including color, hue, saturation, brightness, or sharpness associated with the image and a brightness and/or amount of the one or more stains present in the whole slide image. Depending on the specific types of attributes to be adjusted and/or additional inputs provided by the user, one or more of the stain prediction module 202, the color constancy module 204, the stain adjustment module 206, and the attribute value adjustment module 208 may be implemented to perform the adjustments.

In step 306, the method 300 may include providing the adjusted whole slide image (e.g., adjusted image 212) as output.

Stain Prediction Module

Figure 4A:
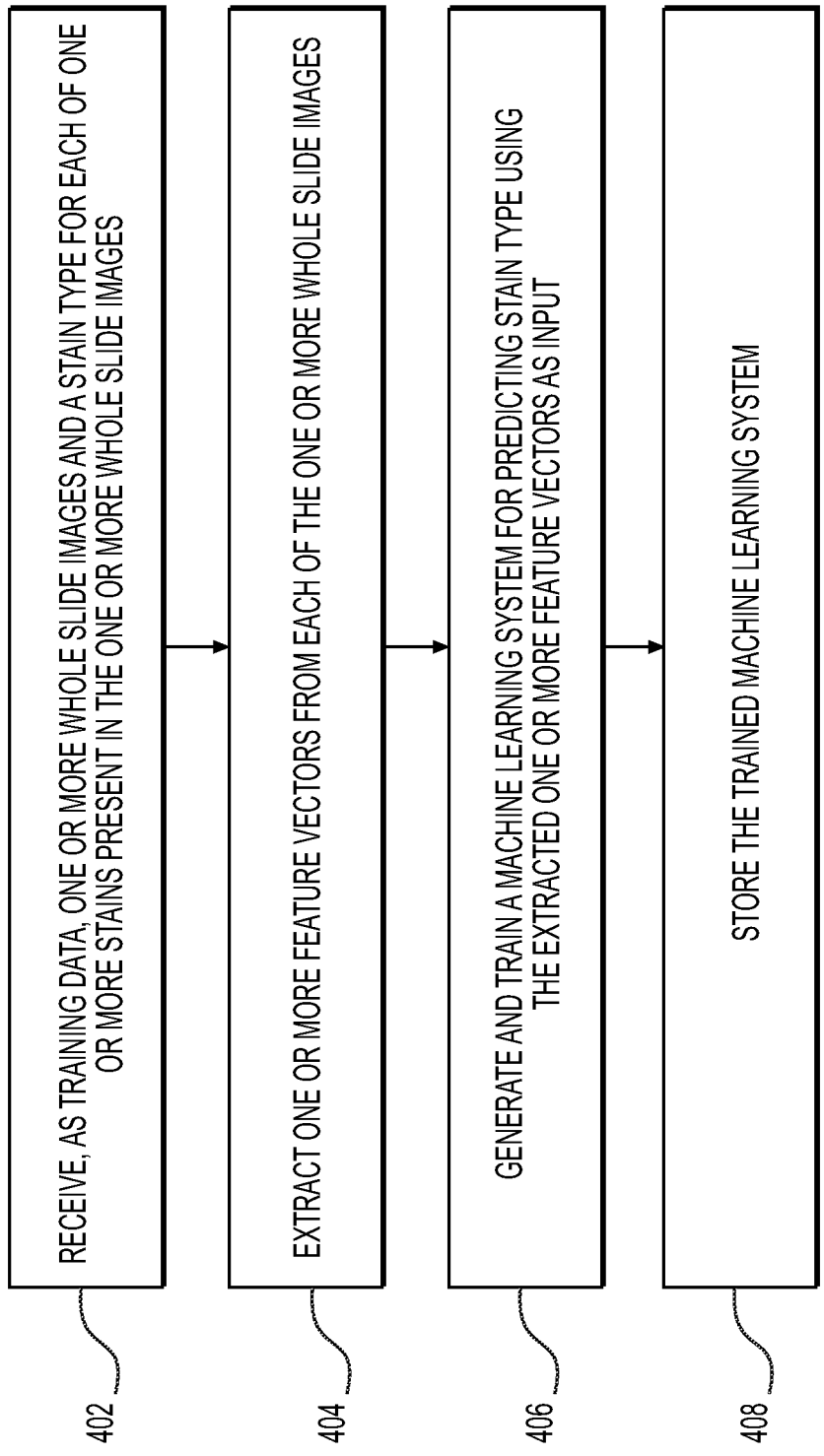
FIG. 4A is a flowchart illustrating an exemplary method for training a stain prediction module, according to an exemplary embodiment of the present disclosure.

FIG. 4A is a flowchart illustrating an exemplary method 400 for training a machine learning system to predict a stain type of one or more stains present in a whole slide image, according to an exemplary embodiment of the present disclosure. The whole slide image may be a digitized image of a slide-mounted pathology specimen, for example. There are numerous types of stains or combination of stains that may be used in the preparation of the pathology specimen. Identifying a stain type of one or more stains used in the preparation may enable or facilitate various types of attribute adjustments to the whole slide image that may be stain specific, including adjustment of a brightness and/or amount of the one or more stains in the whole slide image. The exemplary method 400 (e.g., steps 402-408) may be performed by the training image platform 131 (e.g., by stain type identification module 133) of the slide analysis tool 101. The exemplary method 400 may include one or more of the following steps.

In step 402, the method 400 may include receiving, as training data, one or more whole slide images and a stain type for each of one or more stains present in the one or more whole slide images. The received whole slide images may be training images, whereas the stain type for the stains present in each received whole slide image may form a label corresponding to the respective training image. For example, a first training image may be a whole slide image that includes two stains of a first and second stain type. Therefore, the label corresponding to the respective training image may indicate the first and second stain types.

The whole slide images may be digitized images of stained pathology slides. There are numerous types of stains or combinations of stains that may be used when preparing the slides. To generate a representative dataset of training images, the received whole slide images at 402 may include one or more images having each stain type that may be used in preparation. In some examples, one or more of the whole slide images received as training images may be thumbnails or macro-images.

In step 404, the method 400 may include extracting one or more feature vectors from each of the one or more whole slide images. In some examples, the feature vectors may be extracted from particular regions of the whole slide images corresponding to non-background pixels of the whole slide images. For example, each whole slide image may be comprised of a plurality of tiles, where the tiles include one or more of background pixels and non-background pixels. In one aspect, prior to extracting the feature vectors, the background pixels of the whole slide images may be removed using Otsu's method (e.g., a type of automatic image thresholding that separates pixels into two classes, foreground and background) or by removing tiles, and thus the pixels comprising the tiles, with low variance from the whole slide image. Accordingly, the non-background pixels of the whole slide images remain for feature extraction. In another aspect, prior to extracting the feature vectors, the whole slide images may be converted into a reduced summary form. The reduced summary form may include a collection of non-background RGB pixels of a whole slide image or a set of neighboring non-background pixel patches (or tiles) of a whole slide image. Accordingly, the non-background pixels of the whole slide images remain for feature extraction. In some examples, for obtaining the reduced summary form, the whole slide images may be spitted into a collection image tile or a set of distinct pixels.

The type or format of the feature vector extracted may vary. In one example, the extracted feature vectors may be vectors of RGB pixel values for non-background tiles of the whole slide images. In another example, the extracted feature vectors may be one or more embeddings (e.g., for a convolutional neural network (CNN)) from non-background tiles of the whole slide images. Additionally or alternatively, if one or more of the whole sale images received is a thumbnail (e.g., macro-image), the extracted feature vectors may be a CNN embedding from the thumbnail. In a further example, image classification-based feature generation techniques, such as bag-of-visual words or Vector of Locally Aggregated Descriptors (VLAD), may be applied to convert descriptors from one or more regions of the whole slide image into vectors. The descriptors may include a color scale-invariant feature transform (SIFT) descriptor, an Oriented FAST and rotated BRIEF (ORB) feature, a histogram of oriented gradients (HOG) descriptor, a radiant-invariant feature transform RIFT descriptor and/or a speeded up robust features (SURF) descriptor.

In step 406, the method 400 may include to generate and train a machine learning system for predicting stain type using the extracted feature vectors as input. The machine learning system may include a Naïve Bayes classifier, a random forest model, a convolutional neural network (CNN), a recurrent neural network (RNN) such as a simple RNN, a long short-term memory (LSTM) network, a gated recurrent unit (GRU) or the like, a transformer neural network, and/or a support vector machine, among other similar systems.

As one non-limiting example, extracted feature vectors of a training image may be input to the machine learning system. The machine learning system may predict a stain type for one or more stains present in the training image, and provide the predicted stain type as output. In some examples, for each training image more than one predicted stain type for a given stain may be output by the machine learning system, where each predicted stain type may be associated with a probability or score that represents a likelihood of the respective stain type being the actual stain type for the given stain. For example, for a first stain of a first training image, the machine learning system may output a first stain type associated with an 80% probability of being the stain type and a second stain type associated with a 20% probability of being the stain type.

In one example, to train the machine learning system, the predicted stain type(s) may be compared to the label corresponding to the training image provided as input to determine a loss or error. For example, a predicted stain type for a first stain of a first training image may be compared to the known stain type for the first stain of the first training image identified by the corresponding label. The machine learning system may be modified or altered (e.g., weights and/or bias may be adjusted) based on the error to improve an accuracy of the machine learning system. This process may be repeated for each training image or at least until a determined loss or error is below a predefined threshold. In some examples, some of the training images may with withheld and used to further validate or test the trained machine learning system.

In step 408, the method 400 may include to store the trained machine learning system for subsequent deployment by the stain prediction module 202 of the appearance modifier module 138 described below with reference to FIG. 4B.

Figure 4B:
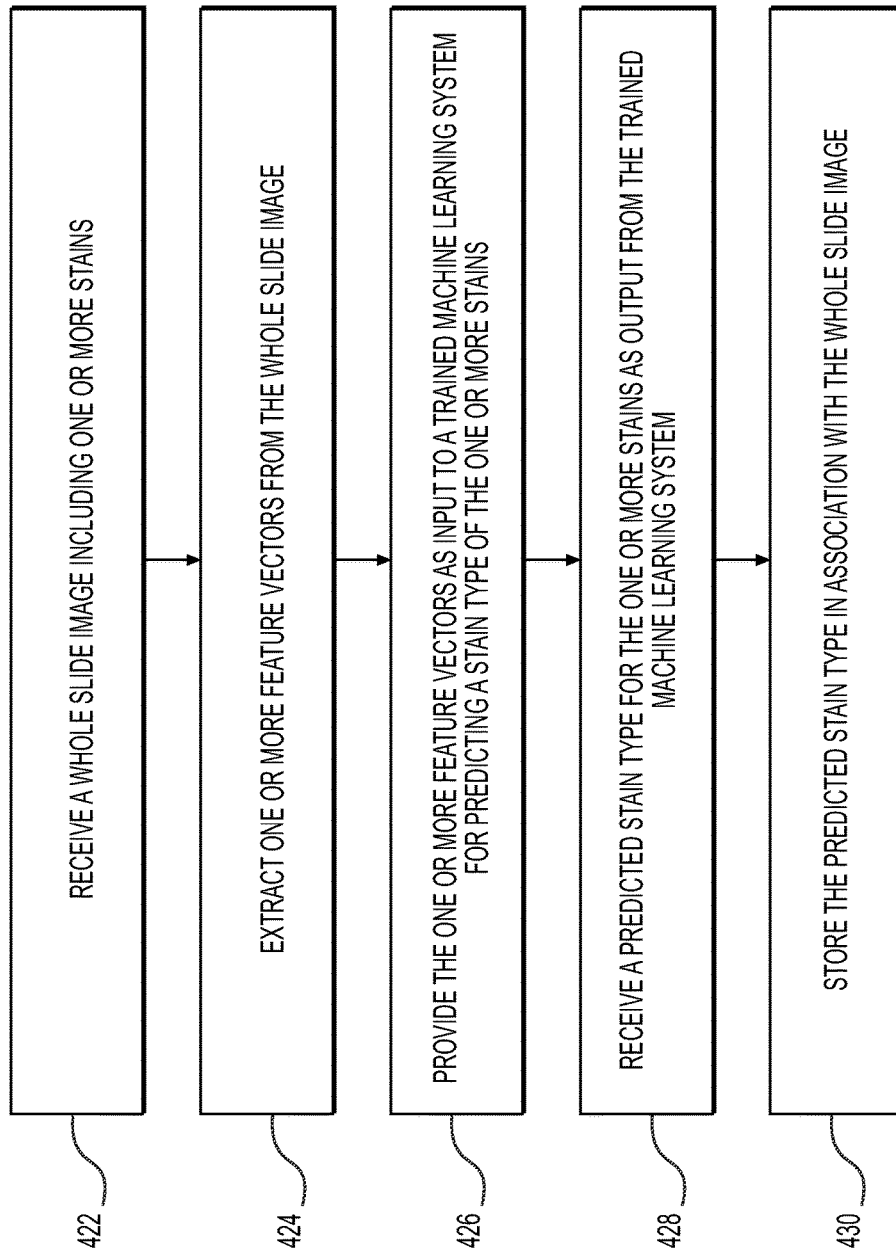
FIG. 4B is a flowchart illustrating an exemplary method for deploying a trained stain prediction module to predict a stain type of one or more stains present in a whole slide image, according to an exemplary embodiment of the present disclosure.

FIG. 4B is a flowchart illustrating an exemplary method 420 for predicting a stain type of one or more stains present in a whole slide image, according to an exemplary embodiment of the present disclosure. The exemplary method 420 (e.g., steps 422-428) may be performed by the target image platform 136 of the slide analysis tool 101, and particularly by the stain prediction module 202, automatically and/or in response to a request from a user (e.g., pathologist, patient, oncologist, technician, administrator, etc.). The exemplary method 400 may include one or more of the following steps.

In step 422, the method 420 may include receiving a whole slide image as input (e.g., input image 210). In some examples, the whole slide image may be a portion of a whole slide image (e.g., one or more regions of interest) or a thumbnail of the whole slide image. The whole slide image may be a digitized image of a pathology slide for which one or more stains were used in the preparation thereof. Accordingly, the one or more stains may be present in the whole slide image. In some examples, the stain type of the one or more stains may be unknown. In other examples, an input stain type for the stains may be received along with the whole slide image. However, it may nonetheless be beneficial to validate or confirm that the input stain type provided is in fact a correct stain type.

In step 424, the method 420 may include extracting one or more feature vectors from the whole slide image. In some examples, the feature vectors may be extracted from non-background pixels of the whole slide image using the same or similar processes described above in conjunction with step 404 of the method 400. In step 426, the method may include providing the one or more feature vectors as input to a trained machine learning system, such as the trained machine learning system described in FIG. 4A, to predict a stain type of the one or more stains present in the whole slide image.

In step 428, the method 400 may include receiving the predicted stain type for the one or more stains of the whole slide image (e.g., predicted stain type 222) as output from the trained machine learning system. In some examples, the predicted stain type may be provided for display in conjunction with the whole slide image through the viewing application tool 108. If more than one predicted stain type is received as output of the trained machine learning system, the predicted stain type having a highest associated probability or score may be selected for display. However, if a probability or score associated with one or more of the predicted stain types output by the trained machine learning system is below a pre-defined threshold, then a notification or alert may be generated and provided to the user to indicate that the stain type is unknown or the stain is of poor quality. Additionally, in instances where an input stain type is received along with the whole slide image, a comparison between the predicted stain type and the input stain type may be performed. If, based on the comparison, a determination is made that the input stain type was erroneous, a notification or alert may be generated and provided for display through the viewing application tool 108.

In step 430, the method 420 includes storing the predicted stain type in association with the whole slide image (e.g., in one of storage devices 109). The predicted stain type may be subsequently retrieved from storage and used as input for one or more other sub-modules of the appearance modifier module 138, such as the stain adjustment module 206 implemented to adjust the one or more stains.

Color Constancy Against Reference or Population of Slides

Figure 5:
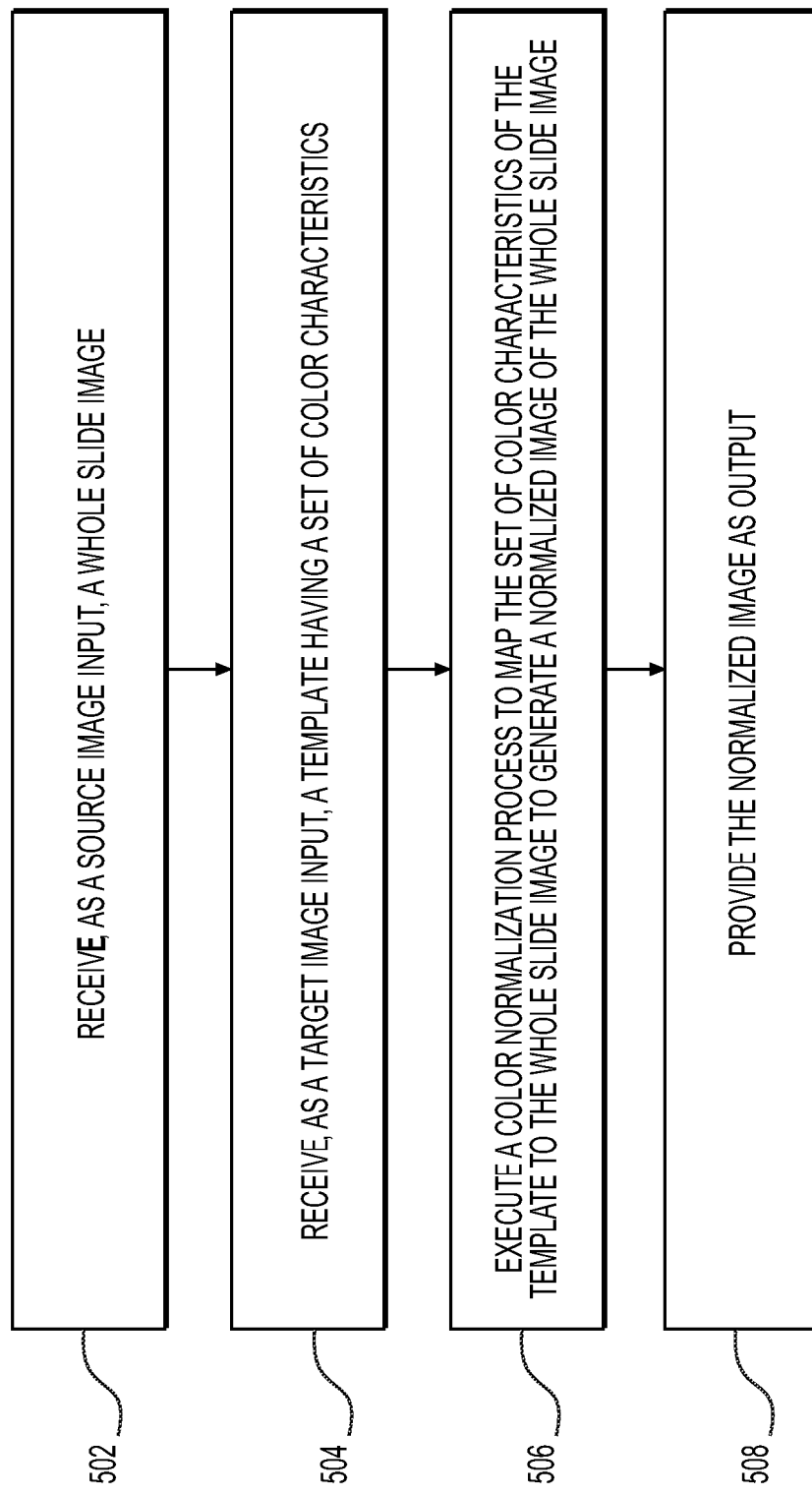
FIG. 5 is a flowchart illustrating an exemplary method for template-based color adjustment of a whole slide image, according to an exemplary embodiment of the present disclosure.

FIG. 5 is a flowchart illustrating an exemplary method 500 of template-based color adjustment of a whole slide image, according to an exemplary embodiment of the present disclosure. Color variations among whole slide images within a set or population being viewed and analyzed by a pathologist in one sitting may be problematic for the pathologist as their eyes may become used to a specific color distribution. For example, one whole slide image might look pinker in color among other images that the pathologist has been reviewing, which may cause differentiation between structures to be less clear. Color variations among whole slide images may result from using different scanners to scan the slides or may arise from a variety of factors related to slide preparation. To address the issue of color variation, the exemplary method 500 (e.g., steps 502-508) may be performed by the slide analysis tool 101, and particularly the color constancy module 204, automatically and/or in response to a request from a user (e.g., pathologist, patient, oncologist, technician, administrator, etc.). The exemplary method 500 may include one or more of the following steps.

In step 502, the method 500 may include receiving a whole slide image for template-based color adjustment. The whole slide image may be a source image input received by the color constancy module 204 of the appearance modifier module 138. The whole slide image may be an original whole slide image received as input to the appearance modifier module 138 (e.g., input image 210). For simplicity and clarity, one whole slide image is discussed. However, in other examples, a plurality of whole slide images to be viewed by a user may be received as input in step 502.

In step 504, the method 500 may include receiving a template having a set of color characteristics (e.g., template 232). The template may be a target image received as additional input to the color constancy module 204. As previously discussed, the whole slide image may include a plurality of tiles. The template may include a tile of a whole slide image, a set of tiles of a whole slide image, an entirety of a whole slide image, or a set of two or more whole slide images. The template may be one of a set of predefined templates stored by the image adjustment platform 100 (e.g., in one of storage devices 109) and selected by the user. In other examples, the template may be uploaded by the user.

In step 506, the method 500 may include executing a color normalization process to map the set of color characteristics of the template to the whole slide image to generate a normalized image of the whole slide image (e.g., normalized image 234). For example, one or more of the machine learning systems, such as the machine learning systems generated by the color normalization module 134, may be deployed or run by the color constancy module 204 to perform the color normalization process based on the source image input and target image input received in steps 502 and 504, respectively. The normalized image may include an adjusted whole slide image having color characteristics that correspond to the color characteristics of the template. In some examples, the template and/or the whole slide image may be in a first color space (e.g., an RGB color space) and the color normalization process may include a conversion of the template and/or the whole slide image to a second color space prior to mapping the set of the color characteristics of the template to the whole slide image. Example second color spaces may include a HSV (hue, saturation, value) color space, a HIS (hue, intensity, saturation) color space, and a L*a*b color space, among other examples. In some examples, one or more regions of the whole slide image(s) received as the template, such as a tissue region, may be segmented out to assure the second color space is constructed based on the stained tissue. That is, the segmented out regions (e.g., the tissue region) may be included as part of the template that is used for color characteristics mapping.

Various types of color normalization processes may be executed by one or more machine learning systems to map or otherwise transfer the color characteristics of the template to the whole slide image. Example color normalization processes may include histogram specification, Reinhard method, Macenko method, stain color descriptor (SCD), complete color normalization, and structure preserving color normalization (SPCN), among other similar processes discussed in turn below.

For implementation of histogram specification, the whole slide image may be converted from a first, RGB color space to a second, L*a*b color space. In the second, Lab color space, a histogram of the whole slide image (e.g., a source image histogram) may be matched to a histogram of the template (e.g. a target image histogram). Following the mapping, the whole slide image may be reconverted back to the first, RGB color space. For implementation of the Reinhard method, the whole slide image and template may be converted from a first, RGB color space to a lap color space, and a linear transformation may be used to match the mean and standard deviations of each color channel in the whole slide image to those of the template prior to reconverting the whole slide image back to the RGB color space. For implementation of the Macenko method, the whole slide image may be converted from a first, RGB color space to an optical density (OD) space. Within the OD space a singular value decomposition (SVD) may be identified and a plane corresponding to its two largest singular values may be created. Data may be projected onto that plane, and corresponding angles may be found. The maximum and minimum angle may be estimated, and those extreme values may then be projected back to the OD space.

For implementation of SCD, the whole slide image may be converted from a first, RGB color space to a second, OD space. A stain color appearance matrix (S) may be empirically found by measuring a relative color proportion for R, G and B channels, and a stain depth matrix may be estimated by taking the inverse of S, multiplied with intensity values in OD, similar to the Ruifrok method. For implementation of SPCN, the whole slide image (e.g., a source image) and template (e.g., a target image) may be factorized into a color appearance matrix (S) and a stain depth matrix (C) by non-negative matrix factorization (NMF), where at least multiple co-efficients of S and C are positive. The stain depth matrix of the source image may be combined with the color appearance matrix of the target image to generate a normalized source image.

Alternative color normalization process implemented may further include the following processes discussed in turn below. Joint Approximate Diagonalization of Eigenmetrices (JADE) may be implemented to recover an independent component for independent component analysis (ICA) decomposition. Blind color decomposition may be implemented to separate intensity information from color information. For example, the images may be converted from a first, RGB color space to a second, Maxwellian color space to estimate a color distribution of separate stains. Reference color vectors may be identified, and, by linear decomposition, stain absorption vectors may be estimated and used to adjust color variation. A hue-saturation-density (HSD) model for stain recognition and mapping may be implemented. Initially the whole slide image may be converted from a first, RGB color space to a second, hue-saturation-intensity (HIS) model, where the HSD model may be defined as the RGB to HIS transform. HSI data has two chromatic components and a density component. Different objects that correspond to different stains (e.g., nuclei, background) may be segmented before obtaining the chromatic and density distribution of hematoxylin, eosin and background. The contribution of stain for every pixel may be weighted as needed. The HSD model may then be transformed back to the RGB color space. Style transfer models may alternatively be implemented to transfer color characteristics of one image to another.

Additionally, the color normalization processes may be implemented by one or more types of generative adversarial network (GAN)-based machine learning systems. As one example, an Information Maximizing Generative Adversarial Network (InfoGAN) and learning control variables automatically learned by the model may be implemented, where the control variables may be used to mimic color characteristics in the template. As another example, histoGAN, a color histogram-based method for controlling GAN-generated images' colors and mapping each color to the color of a target image (e.g., the template) may be implemented. As a further example, CycleGAN may be implemented to learn a style of a group of images (e.g., learn style of the template).

In step 508, the method 500 may include providing the normalized image (e.g., the normalized image 234) as output of the color constancy module 204. The normalized image may be an adjusted whole slide image having color characteristics corresponding to the set of color characteristics of the template as a result of the color normalization process. In some examples the normalized image may be the adjusted image 212 output by the appearance modifier module 138. In other examples, the normalized image may be provided as input into other sub-modules of the appearance modifier module 138, including the stain adjustment module 206 or the attribute value adjustment module 208.

Semantically Meaningful Stain Adjustment

As exemplified by the above discussion with reference to FIG. 5, adjustment of color attributes of a whole slide image, such as brightness, hue, and saturation, may not be done in a sensible manner using an original RGB color space of the whole slide image. Therefore, the whole slide image may be converted to alternative color spaces in which the adjustments can be made. Similarly, for adjusting one or more color properties of a stain, which may be particularly important if overstaining or understaining has occurred, the image may need to first be converted from the original RGB color space to a color space specific to a stain type (e.g., a stain-specific color space). However, unlike hue, saturation, and brightness attributes of the whole slide image, it may not be possible to simply define the stain-based quantifications up front to perform such conversion. Instead, as part of the training image platform 131, one or more machine learning systems may be built (e.g., by the color space transformation module 135) for learning a transformation that enables conversion of the whole slide image from the original, RGB color space to the stain-specific color space.

Various types of machine learning systems may be utilized to learn the transformation. The transformation may include linear and non-linear transformations. Transformations may be learned for a plurality of different stain types. For example, a transformation may be learned for each stain type or combination of stain types that may be utilized for staining pathology slides. In some examples, a machine learning system specific to each stain type or combination may be built. In other examples, one machine learning system may be capable of learning transformations for more than one stain type or combination. The learned transformations may then be stored in a data store (e.g., in one of storage devices 109) in association with the specific stain type or combination of stain types for subsequent retrieval and application when adjusting one or more stain properties of a whole slide image, as described in detail with reference to FIG. 6.

One specific but non-limiting example of a learned transformation may include a learned, invertible linear transformation of a whole slide image from an RGB color space to a stain color space. The whole slide image may include two stains of hematoxylin and eosin. This example transformation may be described by a stain matrix. For example, assuming the whole slide image is in an RGB color space, the learned transformation may be given by the matrix multiplication, $$p = T \begin{pmatrix} R \\ G \\ B \end{pmatrix}.$$

R, G, and B may be non-background pixels of the whole slide image in the RGB color space, and T may be an invertible or pseudoinvertible c×3 matrix that converts from the RGB color space to the c-dimensional stain space (p). A number of channels (c) in the c-dimensional stain space (p) may be based on the one or more stain types present in the whole slide image. For example, when the two stains include hematoxylin and eosin, c=3, with a first channel indicating intensity, a second channel indicating hematoxylin, and a third channel indicating eosin. As a further example, if saffron staining is used in conjunction with hematoxylin and eosin for staining, as is common in France, c=4. The rows of T, referred to as vectors or stain vectors, may describe how to convert the pixel values of the whole slide image in the RGB color space (e.g., from red, green and blue channels) to channels in a stain-specific color space. When a whole slide image stained with hematoxylin and eosin is received as input to the stain adjustment module 206, T may be retrieved as the machine-learned transformation for application to at least a portion of the whole slide image to convert the portion of the whole slide image from the RGB color space to the color space specific to hematoxylin and eosin. Conversion to this stain-specific color space may then facilitate adjustments to one or more of the brightness or amount of hematoxylin and/or eosin.

Various types of machine learning systems may be utilized to learn the transformation. In some examples, a principal component analysis (PCA), zero-phase analysis (ZCA), non-negative matrix factorization (NMF), and/or independent components analysis (ICA) may be applied to a subset of non-background RGB pixels from a training set of whole image slides having a given stain or combination of stains to acquire at least the transformation matrix T for the given stain or combination of stains. Subsequently, semantic labels may be applied to one or more rows (e.g., vectors) of the matrix T. Often the first vector may include brightness and the other two vectors may include other stains. The semantic meaning of each vector may be determined via analog introspection, or by comparison with a reference set of vectors determined by using a training set of whole image slides stained with only a single stain or by using a small set of annotations for tissues that are predisposed to absorb specific stains. These learning methods may be applicable if there are three input pixel channels as input and one or a combination of two stains. If there are more than two stains, underdetermined variants of these learning methods may be used.

In other examples, a clustering approach may be applied to a subset of non-background RGB pixels from a training set of whole image slides having a given stain or combination of stains to learn at least the transformation matrix T. For example, k-means clustering identifies k prototypes within the data, where k may be set to the number of vectors desired. Alternatives to k-means clustering may include Gaussian mixture models, mean-shift clustering, density-based spatial clustering of applications with noise (DBSCAN), or the like. The semantic meaning of each vector may be determined via manual introspection or comparing to a reference set of vectors determined using slides stained with only a single stain, or by using a small set of annotations for tissues that are predisposed to absorb specific stains.

In further examples, a regression-based machine learning system (e.g., with supervised learning) may be trained to infer the matrix T transformation. For example, a training dataset of whole slide images and labels identifying pixels determined to be canonical (e.g., canonical pixels) for a given stain may be provided as input to build and train the machine learning system. Canonical pixels may be pixels identified as having structures predisposed to bind with each of one or more stains (e.g., a pixel having DNA for which hematoxylin bins to).

Figure 6:
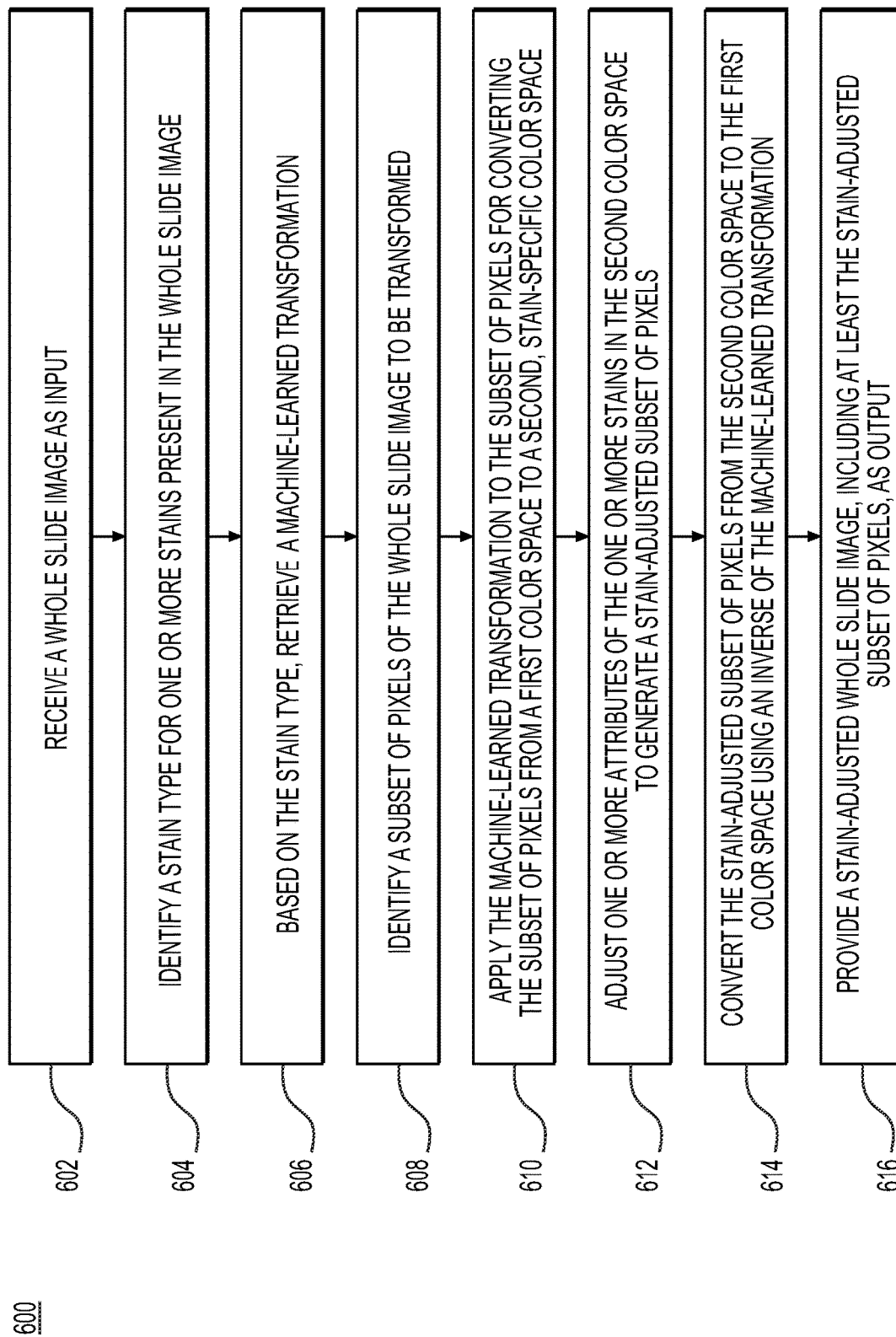
FIG. 6 is a flowchart illustrating an exemplary method for adjusting one or more stains present in a whole slide image, according to an exemplary embodiment of the present disclosure.

FIG. 6 is a flowchart illustrating an exemplary method 600 for performing stain adjustments, according to an exemplary embodiment of the present disclosure. The exemplary method 600 (e.g., steps 602-616) may be performed by the slide analysis tool 101, and particularly the stain adjustment module 206, automatically and/or in response to a request from a user (e.g., pathologist, patient, oncologist, technician, administrator, etc.). The exemplary method 600 may include one or more of the following steps.

In step 602, the method 600 may include receiving a whole slide image (e.g., image 242) as input. The whole slide image may be received as input to the stain adjustment module 206 of the appearance modifier module 138. In some examples, the whole slide image may be the original whole slide image (e.g., input image 210) received by the appearance modifier module 138. In other examples, the whole slide image received as input may be an adjusted version of the original whole slide image output by one or more other modules of the appearance modifier module 138, such as the normalized image output by the color constancy module 204 (e.g., normalized image 234).

An entirety of the whole slide image may be received as input. Alternatively, a portion of the whole slide image may be received as input. The portion may indicate a defined region of interest to which the stain adjustment is to be applied. The defined region of interest may be a region that is specified manually by the user by drawing or setting a boundary box or the like using the viewing application tool 108. As another example, the defined region of interest may be a region in a field of view (e.g., that the user is zoomed in on) on the viewing application tool 108.

In instances where an entirety of the whole slide image is received and the stain adjustment is to be implemented to the entirety of the whole slide image, a thumbnail image (e.g., a reduced size version of lower resolution based on a color sampling of the whole slide image) of the whole slide image may be utilized for subsequent processing steps. However, use of the thumbnail image may be less optimal as small structures with specific stains have a potential of being missed. Therefore, a majority of pixels corresponding to those particular stains may be removed prior to performing subsequent processing on the thumbnail image. As an alternative option, if the stain adjustment is to be implemented to an entirety of the whole slide image, random patches from different locations of the whole slide image may be selected. The randomly selected patches may be uniformly distributed across the whole slide image to ensure enough color information has been obtained. Pixels included within the randomly selected patches may be used for subsequent processing steps.

In step 604, a stain type for a stain present in the whole slide image may be identified. In some examples, the stain type is provided as input along with the whole slide image (e.g., an input stain type). In other examples, the stain type identified may be the predicted stain type output by the stain prediction module 202 (e.g., predicted stain type 222). To provide an illustrative example, hematoxylin and eosin may be the identified combination of stain types present in the whole slide image. Hematoxylin binds to DNA and stains the nuclei a dark blue or purple, whereas eosin stains the extracellular matrix and cytoplasm pink.

In step 606, the method 600 may include retrieving, based on the stain type, a machine-learned transformation. The machine-learned transformation may be retrieved in order to convert the whole slide image from a first color space (e.g., a RGB color space in which the whole slide image was received) to a second color space that is specific to the stain type (e.g., a second, stain-specific color space). For example, a machine-learned transformation that is associated with the stain type may be retrieved from among the plurality of machine-learned transformations stored in the data store (e.g., in one of storage devices 109), the transformations having been learned by one or more machine learning systems generated as part of the training image platform 131 (e.g., by color space transformation module 135). For example, when the whole slide image is identified as being stained with hematoxylin and eosin, the matrix T may be the machine-learned transformation retrieved from the data store.

In step 608, the method 600 may include identifying at least a subset of pixels of the whole slide image to be transformed. The subset of pixels to be transformed may include non-background pixels and non-artifact pixels (e.g., the pixels may include the stain that is being adjusted). Pixels of the whole slide image (or portion thereof) may be classified into background pixels and non-background pixels. Pixels can be determined as background pixels and excluded from the subset using Otsu's method, by analyzing the variance of tiles, or by identifying if a pixel is sufficiently close to a reference white background pixel by fitting a distribution to pixels identified as the background, among other similar techniques. Additionally, some pixels (whether background or non-background) may represent artifacts, such as bubbles, ink, hair, tissue folds, and other unwanted aspects, present on the whole slide image. Artifact pixels may be identified using semantic segmentation, among other similar techniques, and excluded from the subset (e.g., such that non-artifact pixels remain).

In step 610, the method may include applying the machine-learned transformation to the subset of pixels to convert the subset of pixels from a first color space to the second, stain-specific color space. Continuing the example where the whole slide image is stained with hematoxylin and eosin, when the matrix T is retrieved and applied to the subset of pixels, one or more intensities present for a red, green and/or blue channel in the original RGB color space may now be represented as a linear combination of the stains present (e.g., as stain vectors). For example, the stain vectors may include a first channel indicating intensity, a second channel indicating hematoxylin, and a third channel indicating eosin.

In step 612, the method 600 may include adjusting one or more attributes of the one or more stains in the second, stain-specific color space. The adjustable attributes may include a brightness (e.g., by adjusting pixel value intensity) and/or an amount of each of the one or more stains (e.g., by adjusting values of one or more dimensions in the second, stain-specific color space). Brightness may be increased or decreased. Similarly, the amount of a stain may be increased or decreased. These amount-based stain adjustments may correct for overstaining or understaining resulting from the slide preparation. In some examples, the adjustments may be made automatically, where templates or other similar reference images may be used for the adjustment. In other examples, the adjustments may be made based on user input from interactions with GUI control elements provided for display in conjunction with the whole slide image through the viewing application tool 108. Continuing the example where the whole slide image is stained with hematoxylin and eosin and the matrix T is retrieved and applied to the subset of pixels for the transformation, the GUI control elements may correspond to each channel represented by the stain vectors. For example, the GUI control elements may include a slider bar for adjusting brightness, a slider bar for adjusting an amount of hematoxylin, and a slider bar for adjusting an amount of eosin. Other control elements that allow incremental increases and decreases of value, similar to a slider bar, may be used in addition or alternatively to a slider bar. The adjustments may be made uniformly (e.g., increasing the second channel by 10%, etc.).

In step 614, the method may include converting the stain-adjusted subset of pixels from the second color space back to the first color space using an inverse of the machine-learned transformation (e.g., an inverse matrix T may be applied continuing with the example above). In step 616, the method 600 may include providing a stain-adjusted whole slide image, including at least the stain-adjusted subset of pixels, as output (e.g., stain-adjusted image 246). In some examples, at least the background pixels (and in some instances the background pixels and the artifact pixels) that were previously removed may be added to the stain-adjusted subset of pixels to form the stain-adjusted image for output by the stain adjustment module 206. In other examples, the stain-adjusted subset of pixels alone may be output by the stain adjustment module 206.

In some aspects the stain-adjusted image (or normalized-stain adjusted image if previously adjusted by color constancy module 204) may be the adjusted whole slide image output by the appearance modifier module 138 (e.g., adjusted image 212). In other aspects, the stain-adjusted image may be input into one or more other modules of the appearance modifier module 138 for further adjustments. For example, in addition to the automatic template-based attribute adjustments discussed above with reference to FIG. 5 and stain-specific attribute adjustments discussed above with reference to FIG. 6, a user may desire to manually adjust one or more attributes to better understand or visualize a whole slide image.

Attribute Value Adjustment Module

Figure 7:
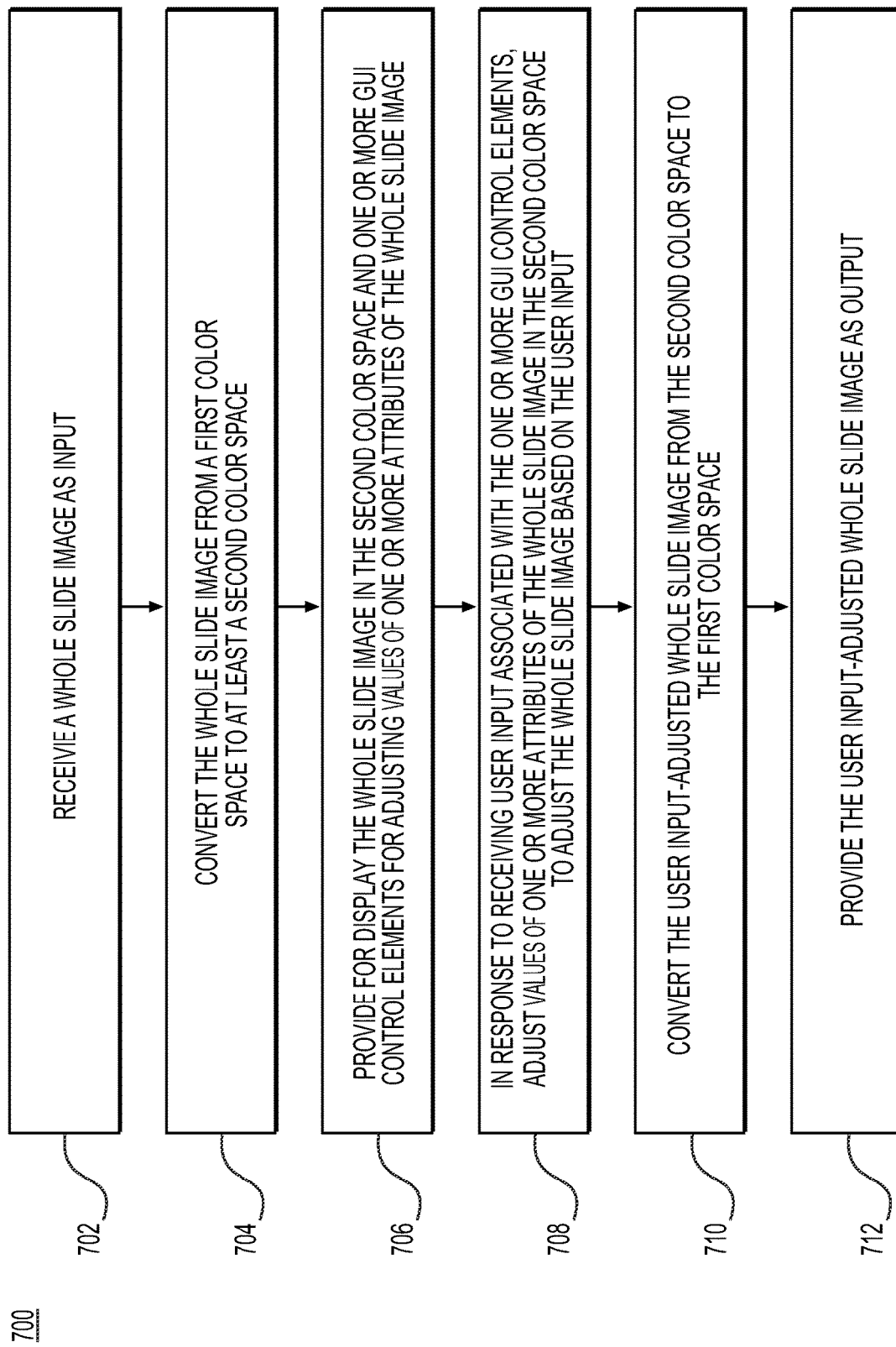
FIG. 7 is a flowchart illustrating an exemplary method for adjusting values of one or more attributes of a whole slide image based on user input, according to an exemplary embodiment of the present disclosure.

FIG. 7 is a flowchart illustrating an exemplary method 700 for enabling attribute value adjustments to a whole slide image based on user input, according to an exemplary embodiment of the present disclosure. The exemplary method 700 (e.g., steps 702-712) may be performed by the slide analysis tool 101, and particularly the attribute value adjustment module 208, automatically and/or in response to a request from a user (e.g., pathologist, patient, oncologist, technician, administrator, etc.). The exemplary method 600 may include one or more of the following steps.

In step 702, the method 700 may include receiving a whole slide image (e.g., image 252) as input to the attribute value adjustment module 208. In some examples, the whole slide image may be the original whole slide image received by the appearance modifier module 138 (e.g., input image 210). In other examples, the whole slide image may be an adjusted version of the original whole slide image. For instance, the whole slide image may be the normalized image 234 output by the color constancy module 204 and/or stain-adjusted image 246 output the stain adjustment module.

The whole slide image may be displayed through the viewing application tool 108 to allow the user to interact with the whole slide image. The whole slide image may be comprised of a large number of pixels. The whole slide image be partitioned into a plurality tiles, each of the tiles including a subset of the pixels. In some examples, one or more of the tiles may be selected or otherwise identified through the viewing application tool 108, and the attribute value adjustment module 208 may receive an indication of the selection. For example, the user may draw a bounding box around the one or more tiles (e.g., associated with a magnification and size). Alternatively, the one or more tiles may be identified based on a field of view (e.g., a zoomed-in region) including the one or more tiles. In such examples, the various attribute value adjustments described in detail below may be carried out on those one or more selected or identified tiles (e.g., at that magnification and size or in the zoomed in region).

In step 704, the whole slide image or at least a portion thereof (e.g., the one or more tiles) may be converted from a first color space in which the image was received (e.g., an RGB color space) to at least one other second color space. The second color space may be an alternative color space in which adjustments to one or more attribute values of the whole slide image may be made. One example second color space may include a Hue-Saturation-Value (HSV) color space. Hue may be used for adjusting color attributes and saturation may be used as a tool to change how much color attributes are diluted with white. In some examples, the whole slide image may be converted into two or more different color spaces (e.g., second, third, and/or fourth color spaces, etc.) to allow a user to make adjustments in more than one alternative color space.

In step 706, the whole slide image in the second color space (or any other alternative color space) and one or more GUI control elements for adjusting values of one or more attributes may be provided for display in a user interface of the viewing application tool 108, for example. The attributes for adjustment may include brightness, sharpness, contrast, and color, among other similar image attributes or properties. Accordingly, GUI control elements associated with brightness, sharpness, contrast, and color may be provided for display. The GUI control elements may be elements, such as slider bars, allowing the user to incrementally adjust values associated with each of the attributes.

Example methods for adjusting sharpness and contrast may include, but are not limited to the use of unsharp masking, highboost filtering, gradients (e.g., first order derivatives), Laplacian (e.g., second order derivatives), fuzzy techniques, bilateral and/or trilateral filters, edge preserving decompositions for multiscale tone and detail manipulation, blind deconvolution (e.g., convolution without a known kernel, median sharpen, non-local means sharpen, contrast enhancement, contrast stretching, intensity level slicing, and histogram Equalization. Adjusting brightness may include changing intensity values, and example methods for such adjustment may include multiplying and/or adding some value to the intensity values. Brightness adjustment may also be performed on a specific stain after obtaining stain channels (e.g., after converting the image to a stain-specific color space as described with reference to FIG. 6).

In step 708, in response to receiving user input associated with one or more of the GUI control elements, the method 700 may include adjusting corresponding values of one or attributes of the whole slide image in the second color space (or other alternative color space) to adjust the whole slide image based on the user input. Steps 706 and 708 may be continuously repeated until the user has completed desired adjustments (e.g., until no further input is received).

In step 710, the method 700 may include converting the user input-adjusted whole slide image from the second color space (or other alternative color space) back to the first color space. In step 712, the method 700 may include providing the user input-adjusted whole slide image as output of the attribute value adjustment module 208 (e.g., user input-adjusted image 256). In some examples, the user input-adjusted whole slide image may be the adjusted image output by the attribute value adjustment module 208 and/or of the appearance modifier module 138 (e.g., adjusted image 212). In other examples, the user input-adjusted whole slide image may be provided as input to one or more other sub-modules of the appearance modifier module 138

Figure 8:
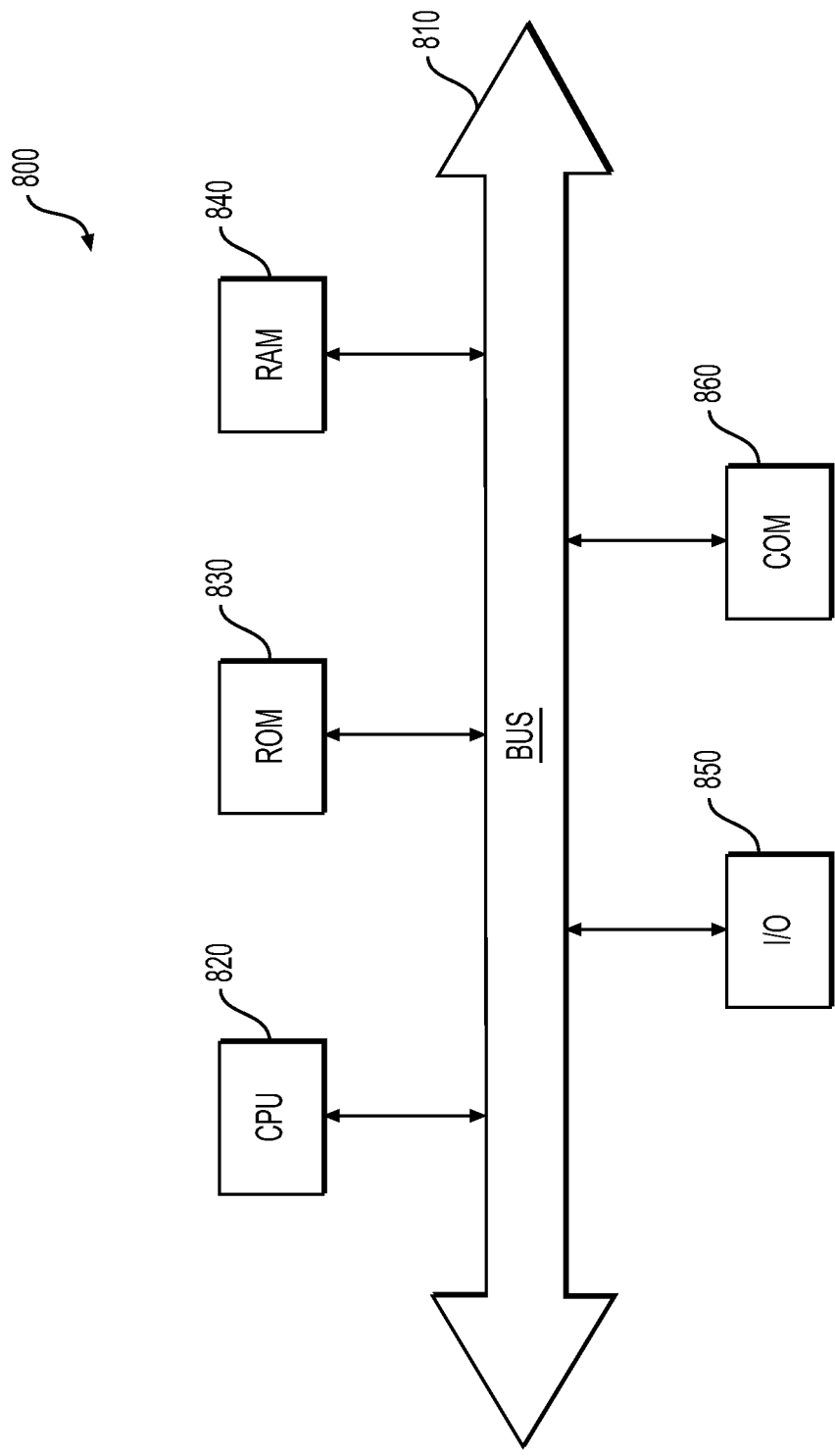
FIG. 8 illustrates an example system that may execute techniques presented herein.

FIG. 8 illustrates an example system or device 800 that may execute techniques presented herein. Device 800 may include a central processing unit (CPU) 820. CPU 820 may be any type of processor device including, for example, any type of special purpose or a general-purpose microprocessor device. As will be appreciated by persons skilled in the relevant art, CPU 820 also may be a single processor in a multi-core/multiprocessor system, such system operating alone, or in a cluster of computing devices operating in a cluster or server farm. CPU 820 may be connected to a data communication infrastructure 810, for example a bus, message queue, network, or multi-core message-passing scheme.

Device 800 may also include a main memory 840, for example, random access memory (RAM), and also may include a secondary memory 830. Secondary memory 830, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 830 may include similar means for allowing computer programs or other instructions to be loaded into device 800. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 800.

Device 800 also may include a communications interface ("COM") 860. Communications interface 860 allows software and data to be transferred between device 800 and external devices. Communications interface 860 may include a modem, a network interface (such as an Ethernet card), a communications port, a PCMCIA slot and card, or the like. Software and data transferred via communications interface 860 may be in the form of signals, which may be electronic, electromagnetic, optical or other signals capable of being received by communications interface 860. These signals may be provided to communications interface 860 via a communications path of device 800, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 800 may also include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

What is claimed is:

1. A system for providing color constancy among whole slide images, the system comprising:
   a processor; and
   a memory coupled to the processor and storing instructions that, when executed by the processor, cause the system to perform operations for:
   receiving, as a source image input to a trained machine learning system, a whole slide image from a population of whole slide images;
   receiving, as a target image input to the trained machine learning system, a template having a set of color characteristics, the template comprising the population of whole slide images;
   executing, by the trained machine learning system, a color normalization process to map the set of color characteristics of the template to the whole slide image to generate a normalized image comprised of the whole slide image adjusted to correspond to the set of color characteristics of the template; and
   providing, as output of the trained machine learning system, the normalized image.

2. The system of claim 1, wherein the set of color characteristics of the template include a hue, a saturation, a brightness, a sharpness, and a contrast associated with the template.

3. The system of claim 1, wherein, prior to the executing of the color normalization process, the system is further caused to perform operations for segmenting one or more regions of one or more whole slide images from the population of whole slide images.

4. The system of claim 1, wherein the whole slide image is received in a first color space, and the system is further caused to perform operations for:
   converting the whole slide image from the first color space to a second color space prior to the executing of the color normalization process; and
   reconverting the whole slide image back to the first color space subsequent to the executing of the color normalization process.

5. The system of claim 1, wherein receiving the template includes receiving a selection of one of a plurality of predefined templates stored in a data store of the system.

6. The system of claim 1, wherein receiving the template includes receiving an uploaded template.

7. The system of claim 1, wherein the system is further caused to perform operations comprising adjusting one or more attributes of one or more stains present in the normalized image, the adjusting facilitated by a machine-learned transformation associated with a stain type of the one or more stains.

8. The system of claim 7, wherein the system is further caused to perform operations comprising identifying the stain type of the one or more stains by:
extracting one or more feature vectors from the whole slide image;
providing the one or more feature vectors as input to a second trained machine learning system for predicting stain types; and
receiving, as output from the second trained machine learning system, a predicted stain type.

9. The system of claim 1, wherein the system is further caused to perform operations comprising:
providing for display the normalized image and a plurality of graphical user interface (GUI) control elements corresponding to one or more of color, brightness, sharpness, or contrast attributes; and
adjusting one or more of the color, brightness, sharpness, or contrast attributes of the normalized image based on received input associated with one or more of the plurality of GUI control elements.

10. A method for providing color constancy among whole slide images, the method comprising:
receiving, as a source image input to a trained machine learning system, a whole slide image from a population of whole slide images;
receiving, as a target image input to the trained machine learning system, a template having a set of color characteristics, the template comprising the population of whole slide images;
executing, by the trained machine learning system, a color normalization process to map the set of color characteristics of the template to the whole slide image to generate a normalized image comprised of the whole slide image adjusted to correspond to the set of color characteristics of the template; and
providing, as output of the trained machine learning system, the normalized image.

11. The method of claim 10, wherein the set of color characteristics of the template include a hue, a saturation, a brightness, a sharpness, and a contrast associated with the template.

12. The method of claim 10, wherein the whole slide image is received in a first color space, and the method further comprises:
converting the whole slide image from the first color space to a second color space prior to the executing of the color normalization process; and
reconverting the whole slide image back to the first color space subsequent to the executing of the color normalization process.

13. The method of claim 10, further comprising:
adjusting one or more attributes of one or more stains present in the normalized image, the adjusting facilitated by a machine-learned transformation associated with a stain type of the one or more stains.

14. The method of claim 13, further comprising:
identifying the stain type of the one or more stains by:
extracting one or more feature vectors from the whole slide image;
providing the one or more feature vectors as input to a second trained machine learning system for predicting stain types; and
receiving, as output from the second trained machine learning system, a predicted stain type.

15. The method of claim 10, further comprising:
providing for display the normalized image and a plurality of graphical user interface (GUI) control elements corresponding to one or more of color, brightness, sharpness, or contrast attributes; and
adjusting one or more of the color, brightness, sharpness, or contrast attributes of the normalized image based on received input associated with one or more of the plurality of GUI control elements.

16. A non-transitory computer-readable medium storing instructions that, when executed by a processor, cause the processor to perform operations for providing color constancy among whole slide images, the operations comprising:
receiving, as a source image input to a trained machine learning system, a whole slide image from a population of whole slide images;
receiving, as a target image input to the trained machine learning system, a template having a set of color characteristics, the template comprising the population of whole slide images;
executing, by the trained machine learning system, a color normalization process to map the set of color characteristics of the template to the whole slide image to generate a normalized image comprised of the whole slide image adjusted to correspond to the set of color characteristics of the template; and
providing, as output of the trained machine learning system, the normalized image.

17. The method of claim 13, wherein for adjusting the one or more attributes of one or more stains present in the normalized image, the machine-learned transformation is applied to a subset of a plurality of pixels of the normalized image, and the method further comprises:
classifying the plurality of pixels into background pixels and non-background pixels; and
identifying one or more pixels of the plurality of pixels representing artifacts as artifact pixels, wherein the subset includes non-background pixels and non-artifact pixels.

18. The method of claim 17, wherein applying the machine-learned transformation to the subset of the plurality of pixels comprises converting the subset from a first color space to a second color space specific to the stain type of the one or more stains present in the normalized image, and adjusting the one or more attributes of the one or more stains, wherein the method further comprises:
providing for display the subset of the plurality of pixels in the second color space and a plurality of graphical user interface (GUI) control elements corresponding to a plurality of attributes of the one or more stains;
receiving input associated with one or more of the plurality of GUI control elements; and
adjusting respective one or more attributes of the one or more stains based on the input.

19. The method of claim 17, wherein the plurality of pixels of the normalized image are a pixel patch from a plurality of pixel patches randomly selected from the normalized image that are uniformly distributed across the normalized image.

20. The method of claim 14, wherein the stain type of the one or more stains is received as an input stain type, and for identifying the stain type of the one or more stains, the method further comprises comparing the input stain type to the predicted stain type to validate the input stain type.

* * * * *